United States Patent
Hasegawa et al.

(10) Patent No.: US 11,487,412 B2
(45) Date of Patent: Nov. 1, 2022

(54) INFORMATION PROCESSING METHOD AND INFORMATION PROCESSING SYSTEM

(71) Applicant: Sony Corporation, Tokyo (JP)

(72) Inventors: Yutaka Hasegawa, Kanagawa (JP); Yoichi Mizutani, Saitama (JP); Masato Kajimoto, Chiba (JP); Masahiro Takahashi, Kanagawa (JP); Hiroshi Kyusojin, Tokyo (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 16/996,452

(22) Filed: Aug. 18, 2020

(65) Prior Publication Data

US 2020/0379633 A1 Dec. 3, 2020

Related U.S. Application Data

(60) Division of application No. 15/458,217, filed on Mar. 14, 2017, now abandoned, which is a continuation of
(Continued)

(30) Foreign Application Priority Data

Jul. 13, 2011 (JP) ................................ 2011-154603

(51) Int. Cl.
*G06F 3/04845* (2022.01)
*H04L 12/18* (2006.01)
(Continued)

(52) U.S. Cl.
CPC ........ *G06F 3/04845* (2013.01); *G06F 3/0484* (2013.01); *G06F 3/1454* (2013.01);
(Continued)

(58) Field of Classification Search
CPC .... G16H 30/40; G16H 80/00; G06F 3/04845; G06F 3/0484; H04M 7/0027
See application file for complete search history.

(56) References Cited

U.S. PATENT DOCUMENTS

| | | | |
|---|---|---|---|
| 2002/0106119 A1* | 8/2002 | Foran .................... | G16H 30/20 382/133 |
| 2002/0138624 A1 | 9/2002 | Esenther | |

(Continued)

FOREIGN PATENT DOCUMENTS

| | | |
|---|---|---|
| JP | H06-161956 A | 6/1994 |
| JP | H07-298235 A | 11/1995 |

(Continued)

OTHER PUBLICATIONS

Office Action issued in connection with Japanese application No. 2011-154603, dated Jun. 2, 2015 (4 pages).

(Continued)

*Primary Examiner* — Mong-Shune Chung
(74) *Attorney, Agent, or Firm* — K&L Gates LLP

(57) ABSTRACT

An information processing system and a method for operating same are provided. The information processing system includes a first information processing apparatus and a second information processing apparatus. The first information processing apparatus is configured to display a first synchronous image in a first window, the first window having an operation right. The second information processing apparatus has a synchronous state or an asynchronous state. The second information processing apparatus is configured to: display a second synchronous image; in response to a first request, switch from the synchronous state to the asynchronous state; and in response to a second request, switch from the asynchronous state to the synchronous state.

15 Claims, 23 Drawing Sheets

Related U.S. Application Data application No. 13/538,560, filed on Jun. 29, 2012, now Pat. No. 9,635,313.

(51) Int. Cl.
  *H04L 65/403* (2022.01)
  *G16H 30/40* (2018.01)
  *G06F 3/0484* (2022.01)
  *H04N 7/15* (2006.01)
  *G06F 3/14* (2006.01)
  *G06Q 10/10* (2012.01)
  *G06F 16/438* (2019.01)

(52) U.S. Cl.
  CPC ......... *G16H 30/40* (2018.01); *H04L 12/1813* (2013.01); *H04L 12/1827* (2013.01); *H04L 65/403* (2013.01); *H04N 7/15* (2013.01); *G06F 16/4393* (2019.01); *G06F 2203/04803* (2013.01); *G06F 2203/04806* (2013.01); *G06Q 10/10* (2013.01); *H04L 12/1822* (2013.01); *H04M 2250/62* (2013.01)

(56) References Cited

U.S. PATENT DOCUMENTS

| | | | |
|---|---|---|---|
| 2004/0167806 A1* | 8/2004 | Eichhorn | G02B 21/26 382/133 |
| 2005/0162384 A1 | 7/2005 | Yokoyama | |
| 2006/0064396 A1 | 3/2006 | Wei | |
| 2006/0136441 A1 | 6/2006 | Fujisaki | |
| 2006/0184872 A1 | 8/2006 | Dontcheva et al. | |
| 2008/0148167 A1 | 6/2008 | Russak | |
| 2009/0287790 A1 | 11/2009 | Upton et al. | |
| 2009/0327425 A1 | 12/2009 | Gudipaty | |
| 2010/0131873 A1 | 5/2010 | Mejia | |
| 2010/0153497 A1 | 6/2010 | Sylvain et al. | |
| 2010/0312897 A1 | 12/2010 | Allen et al. | |
| 2011/0047485 A1 | 2/2011 | Takakura | |
| 2011/0110576 A1* | 5/2011 | Kreeger | G16H 50/20 382/132 |
| 2011/0126127 A1 | 5/2011 | Mariotti et al. | |
| 2011/0129135 A1* | 6/2011 | Mizutani | G06T 11/60 382/128 |
| 2011/0154266 A1 | 6/2011 | Friend et al. | |
| 2011/0234630 A1* | 9/2011 | Batman | G06F 3/0484 345/629 |
| 2011/0238618 A1* | 9/2011 | Valdiserri | G16H 30/40 707/608 |
| 2011/0282686 A1* | 11/2011 | Venon | G16H 80/00 715/753 |
| 2012/0030288 A1 | 2/2012 | Burckart | |
| 2015/0347682 A1* | 12/2015 | Chen | G16H 50/20 705/2 |
| 2016/0117817 A1* | 4/2016 | Seel | A61B 34/10 382/131 |
| 2017/0180674 A1* | 6/2017 | Wang | A61B 1/041 |

FOREIGN PATENT DOCUMENTS

| | | |
|---|---|---|
| JP | H07333522 | 12/1995 |
| JP | H08-147391 A | 6/1996 |
| JP | 09-198227 | 7/1997 |
| JP | 2000-099233 A | 4/2000 |
| JP | 2003216133 | 7/2003 |
| JP | 2004-005396 A | 1/2004 |
| JP | 2005-286972 A | 10/2005 |
| JP | 2006-092573 A | 4/2006 |
| JP | 3821170 B2 | 9/2006 |
| JP | 2008-040703 | 2/2008 |
| JP | 2008-047122 A | 2/2008 |
| JP | 2009-044265 A | 2/2009 |
| JP | 2009-289022 A | 12/2009 |
| JP | 2010-033229 A | 2/2010 |
| JP | 2010-061678 | 3/2010 |
| JP | 20110072381 | 4/2011 |
| JP | 2011-118479 | 6/2011 |

OTHER PUBLICATIONS

European Patent Office, Extended European Search Report for European Patent Application No. 12004641.2 (related to above-captioned patent application), dated May 24, 2017.

Japan Patent Office, Office Action for Japanese Patent Application No. 2016-027037 (related to above-captioned patent application), dated May 9, 2017.

Japanese Office Action dated Apr. 3, 2018 for Application No. 2016-027037 (7 pages).

Japanese Office Action dated Aug. 28, 2018 for Application No. 2016-027037 (1 page).

Japanese Office Action dated Mar. 5, 2019 for Application No. 2018-122049 (16 pages).

Design of Multipoint Medical Teleconferencing System Using Super High Definition Imaging System; Yamaguchi et al.; NIT Network Innovation Laboratories; 2003; retrieved Mar. 5, 2019; pp. 31-39.

A Computer Supported Collaborative Learning Environment for Knowledge Creation, Store and Transfer in Power System Education; Tanaka et al.; Nov. 20, 1995; pp. 1455-1461.

ASP/IDC; vol. 13 No. 10 2002; Oct. 20, 2002; pp. 8-12.

Japanese Office Action issued in related Japanese Patent Application No. 2018-122049 dated Jun. 4, 2019 and English translation of same. 14 pages.

Masayuki Hashimoto, Current Status and Future of ASP / IDC in Medical Field, Medical Care & Computer (vol. 13, No. 10), Japan, Electronic Publishing Japan Co., Oct. 20, 2002, vol. 13, No. 10, pp. 8-12.

Japan Patent Office, Office Action for Japanese Patent Application No. 2016-027037 (related to above-captioned patent application), dated Oct. 24, 2017.

\* cited by examiner

| Viewer ID | Window ID | Operation right flag | Asynchronous flag |
|---|---|---|---|
| 0001 | 01 | 1 | 0 |
| 0002 | 01 | 0 | 0 |

FIG.3

| Viewer ID | Window ID | Operation right flag | Asynchronous flag |
|---|---|---|---|
| 0001 | 01 | 1 | 0 |
| 0001 | 02 | 0 | 0 |
| 0002 | 01 | 0 | 0 |
| 0002 | 02 | 1 | 0 |

| Viewer ID | Window ID | Operation right flag | Asynchronous flag |
|---|---|---|---|
| 0001 | 01 | 1 | 0 |
| 0001 | 02 | 0 | 0 |
| 0001 | 03 | 0 | 0 |
| 0002 | 01 | 0 | 0 |
| 0002 | 02 | 1 | 0 |
| 0002 | 03 | 1 | 0 |

INFORMATION PROCESSING METHOD AND INFORMATION PROCESSING SYSTEM

CROSS-REFERENCE TO RELATED APPLICATIONS

The present application is a divisional of U.S. application Ser. No. 15/458,217, filed on Mar. 14, 2017, which is a continuation of U.S. application Ser. No. 13/538,560, filed Jun. 29, 2012, which claims priority to Japanese Application No. 2011-154603, filed Jul. 13, 2011, the disclosures of which are hereby incorporated by reference.

BACKGROUND

The present disclosure relates to an information processing method and an information processing system with which users of a plurality of information processing apparatuses share and examine the same image.

There is known a system in which a common screen is shared, as a shared information resource, by terminals of the respective users in order to assist a teleconference between a plurality of users. A videoconference system is an example of such a system. Further, also in the field of pathology, a common pathological image is shared by terminals of a plurality of doctors. Opinions are exchanged between the terminals, and, at the same time, the diagnosis is made. In this manner, diagnosis efficiency is increased.

Further, the following technology is known (For example, see Japanese Patent Application Laid-open No. H07-298235, hereinafter referred to as Patent Document 1). In the technology, a pointing cursor may be displayed on a screen shared by a plurality of terminals. The terminal having a voice, out of a plurality of terminals, holds an operation right of the pointing cursor.

Further, there is known a cooperative examination assisting method in which the same examination information (chest X-ray radiograph) is displayed in the respective display devices of the two examination terminals. Therefore, two doctors may examine the same image. In the cooperative examination assisting method, in order to clarify the focal site, one examination terminal displays an image subjected to pre-emphasis file processing in the display device of this terminal. In addition, the examination terminal transfers editorial processing information to the other examination terminal. Based on the received editorial processing information, the other examination terminal performs pre-emphasis file processing on the image. The other examination terminal displays the result in the display device of this terminal. As a result, the respective doctors of the two examination terminals may share the same editorial processing result (For example, see Japanese Patent Application Laid-open No. H08-147391 (FIG. 2 and paragraphs 0027-0033), hereinafter referred to as Patent Document 2).

SUMMARY

However, in the system where the same image is shared by a plurality of terminals and opinions are exchanged, there are still many problems to be solved. For example, in a case where the resolution of the entire image is higher than the resolution of the screen, a user moves the area, to which the user pays attention, in the entire image. At the same time, the user examines the area. However, during that time, a user having no operation right may find an area that he wishes to examine on his own accord. Even in such a case, it is not possible for the user having no operation right to examine this area as needed, as long as the user exchanges the operation right with the user having the operation right. Further, in a situation where an operation right is exchanged between users at will, image examination is interrupted frequently from the viewpoints of the respective users. There is a fear that it diminishes efficiency, actually.

It is desirable to provide an information processing method and an information processing system which may increase image examination efficiency in a case of sharing the image by users of a plurality of information processing apparatuses.

According to an embodiment of the present disclosure, there is provided an information processing method, including: causing a first information processing apparatus to display a first synchronous image in a first window, the first window having an operation right; causing a second information processing apparatus to display a second synchronous image, the second information processing apparatus having a synchronous state or an asynchronous state; in response to a first request, causing the second information processing apparatus to switch from the synchronous state to the asynchronous state; and in response to a second request, causing the second information processing apparatus to switch from the asynchronous state to the synchronous state.

According to the information processing method of one embodiment of the present disclosure, a user of an information processing apparatus, to which the operation right is not granted, instructs to arbitrarily change image synchronous on/off states of an information processing apparatus, to which the operation right is not granted. Therefore, the user of the information processing apparatus, to which the operation right is not granted, not only passively examines image operation results by a user of an information processing apparatus, to which the operation right is granted, but also actively performs image operations to thereby perform examinations from the other point of view. Further, it is possible to re-establish the image synchronous state as needed. Therefore, a user of an information processing apparatus, to which the operation right is not granted, may operate an image at will without awareness of how to return to the original state, the latest image operation result by a user of an information processing apparatus, to which the operation right is granted, and the like.

The information processing method may further include canceling, in a case where the first request is input by a user, the image synchronous state in the information processing apparatus, the first request being an occurrence of an input by a user for operating an image displayed in the display unit of the information processing apparatus, to which the operation right is not granted. As a result, an operation is input, by a user, in an image, the exclusive operation right to which is not granted to the user. Because such an operation occurs, the user of the information processing apparatus may use the image, the exclusive operation right to which is not granted to the user, as a private image. Further, the operation to the image, the exclusive operation right to which is not granted to the user, starts. At the same time, operations such as moves, zoom factor changes, and the like with respect to the private image are enabled. That is, it is not necessary to perform a user operation only to move to operations with respect to a private image. Therefore, the user operability is further increased.

The information processing method may further include granting, in a case where an operation right acquisition request is input, by a user, in the information processing apparatus, to which the operation right is not granted, the operation right to the information processing apparatus. As a result, according to instructions by users of the respective information processing apparatuses, the image operation right may be moved between the plurality of information processing apparatuses, at will. That is, it is possible to change the image operation side and the side that merely examines the operated image, as needed.

The information processing method may further include: displaying a plurality of images in each of the display units, the images being asynchronous, the images being synchronous with the images in the plurality of information processing apparatuses, respectively; and granting the operation right to one of a plurality of information processing apparatuses, for each synchronous image combination in the plurality of information processing apparatuses.

As a result, with regard to the same or different two images, the respective information processing apparatuses may display, for example, one image as an image to be operated and the other image as an image to be merely examined, and the like. Further, because of this, a plurality of users may interactively and efficiently exchange opinions by using the two images, the operation rights of which are granted to the different users.

The information processing method may further include replacing, in a state where an operation right to one image of a plurality of images displayed in each of the display units is granted to one information processing apparatus, and where an operation right to the other image is granted to the other information processing apparatus, in a case where a third request is input in the other information processing apparatus by a user, the one image with the other image.

For example, the user of one information processing apparatus is a student, and the user of the other information processing apparatus is a teacher. In this case, the display unit of the student-side information processing apparatus may promptly replace the image, the operation right to which is granted to the student side, with the image, the operation right to which is granted to the teacher at present. As a result, the student may operate the image, the operation right to which is granted to the student himself, to thereby confirm the area in the vicinity of the image, the operation right to which is granted to the teacher at present, and the details of the image. Therefore, the student may swiftly start to confirm the area in the vicinity of the image, to which the teacher pays attention at present, and the details of the image, by using the image, the operation right to which is granted to the student side.

According to another embodiment of the present disclosure, there is provided an information processing system, including a plurality of information processing apparatuses. A first information processing apparatus is configured to display a first synchronous image in a first window, the first window having an operation right. A second information processing apparatus has a synchronous state or an asynchronous state. The second information processing apparatus is configured to: display a second synchronous image; in response to a first request, switch from the synchronous state to the asynchronous state; and in response to a second request, switch from the asynchronous state to the synchronous state.

As described above, the present disclosure may increase image examination efficiency in a case of sharing the image by users of a plurality of information processing apparatuses.

These and other objects, features and advantages of the present disclosure will become more apparent in light of the following detailed description of best mode embodiments thereof, as illustrated in the accompanying drawings.

Additional features and advantages are described herein, and will be apparent from the following Detailed Description and the figures.

BRIEF DESCRIPTION OF THE FIGURES

FIG. 3 is a diagram showing the structure of a synchronous control table in a single-window display mode;

FIG. 4 is a diagram showing the structure of the synchronous control table in a multi-window display mode;

FIG. 5 is a diagram showing the structure of the synchronous control table in the multi-window display mode in a case where the number of windows displayed on each viewer is three;

DETAILED DESCRIPTION

Hereinafter, an embodiment of the present disclosure will be described with reference to the drawings.

First Embodiment

[Information Processing System]

Figure 1:
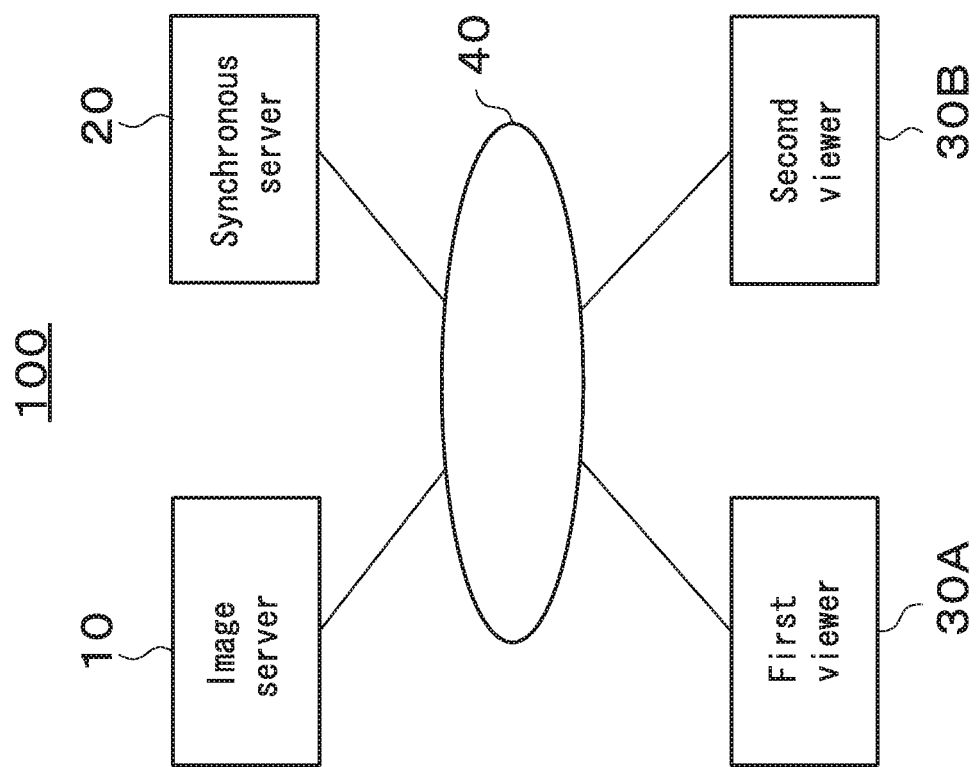
FIG. 1 is a diagram showing the configuration of an information processing system according to a first embodiment of the present disclosure.

FIG. 1 is a diagram showing the configuration of an information processing system according to a first embodiment of the present disclosure.

An information processing system 100 includes an image server 10, a synchronous server 20, and a plurality of viewers 30A, 30B (information processing apparatuses). They may be connected to each other via a network 40. The network 40 may be a WAN (Wide Area Network) such as the Internet, or a LAN (Local Area Network). Further, the network 40 may be wired or wireless. Here, for ease of explanation, the situation where the two viewers 30A, 30B are connected is illustrated. However, the number of viewers may be three or more. In the specification, in a case of identifying the viewers, the respective terms "first viewer 30A" and "second viewer 30B" will be used. In the case of not identifying the viewers, the term "viewer(s) 30A, 30B" will be used.

The image server 10 may be configured by, for example, a general computer. The image server 10 has image storage for storing image data. In response to requests from the viewers 30A, 30B, the image server 10 reads appropriate image data from the image storage and replies the image data to the viewers 30A, 30B. Here, images stored in the image storage may be, for example, microscope images of pathological specimens and the like. A microscope image of a pathological specimen has a resolution higher than that of the screen of the display unit of the viewer 30A, 30B. The image server 10 receives an image data request including, for example, an image name, image location information in the entire image, and the like, from the viewers 30A, 30B. The image server 10 reads appropriate image data from the image storage, and replies the image data to the viewers 30A, 30B. The image location information may be, for example, coordinate data of the image in an entire image. Alternatively, an entire image is divided and handled in a unit of so-called "tile" having a predetermined number of pixels in width and height (For example, 256×256 (pixels), 236×512 (pixels)). In this case, the preassigned number for each unit may be used as the image location information.

[Synchronous Server 20]

The synchronous server 20 performs synchronous processing. In the synchronous processing, the viewers 30A, 30B display the same image. Here, "the same image" means the image of the same area of the same object image in the same zoom factor and the same angle. That is, the image that users of the viewers 30A, 30B watch in the same way is called "the same image".

The synchronous server 20 may be configured by, for example, a general computer system.

Figure 2:
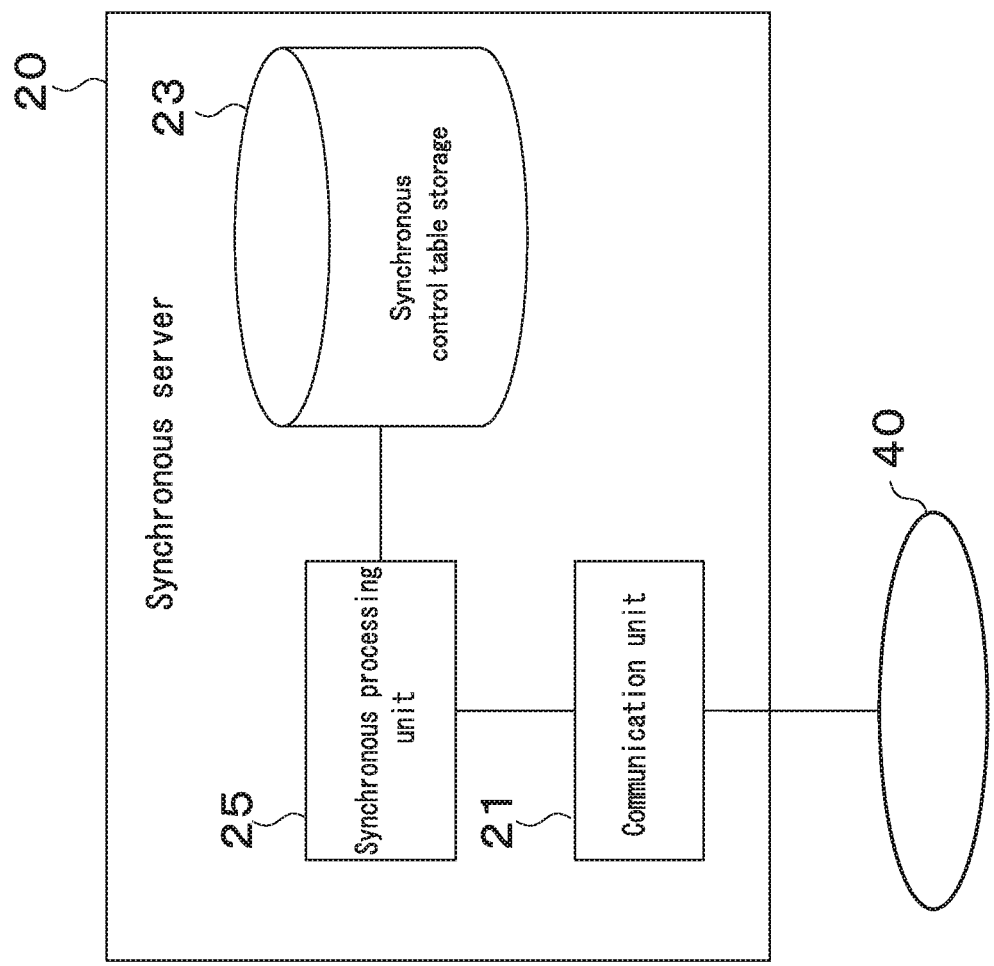
FIG. 2 is a block diagram showing the functional structure of a synchronous server of FIG. 1.

FIG. 2 is a block diagram showing a functional structure of the synchronous server 20 implemented by using a general computer system. As shown in FIG. 2, the synchronous server 20 includes a communication unit 21, synchronous control table storage 23, a synchronous processing unit 25, and the like.

The communication unit 21 receives an image data request, an operation right acquisition request, an asynchronous request, and a synchronous return request from the viewers 30A, 30B via the network 40. The communication unit 21 sends replies to the respective requests to the viewers 30A, 30B via the network 40.

The synchronous control table storage 23 stores synchronous control table. The synchronous control table is control information necessary for image synchronous processing of the viewers 30A, 30B.

FIG. 3 is a diagram showing the structure of the synchronous control table.

In the synchronous control table, records of the respective windows are registered. The number of records is the same as the number of the windows. The record for each window includes information on a viewer ID, a window ID, an operation right flag, an asynchronous flag, and the like. Hereinbelow, the respective information will be described.

The viewer ID is information for identifying a viewer.

The window ID is an ID uniquely given to a combination of a plurality of windows in a correspondence relation. The correspondence relation means that the plurality of windows are image synchronous processing targets of a plurality of viewers. FIG. 3 shows a case where one window is displayed in each of two viewers (single-window display mode). Therefore, the kind of window ID is "01". In a case where a plurality of windows are displayed in each viewer (multi-window display mode), as shown in FIG. 4, there are a plurality of window combinations of a plurality of viewers in a correspondence relation. Therefore, there are a plurality of kinds of window ID, too. Note that the number of windows displayed in each viewer may be three or more. FIG. 5 shows an example of a synchronous control table in this case. The number of the kinds of window ID is three or more.

The operation right flag is a flag for identifying one window to which an exclusive operation right (hereinafter, simply referred to as "operation right".) is given in a combination of a plurality of windows of a plurality of viewers in a correspondence relation. The operation right flag is set for any one window in the combination of a plurality of windows of a plurality of viewers in a correspondence relation. The operation right is a right to perform operations such as moves, zoom factor changes, rotations, and the like (hereinafter, referred to as "image operation".) with respect to an image displayed in a window, according to instructions input by a user. Therefore, an operation, instructed by a user with respect to an image displayed in a window, to which the operation right is not granted, is disabled. Note that, in a case where a temporary asynchronous state is set, the restriction is canceled. The temporary asynchronous state will be described later in detail.

The image operation results in the window, to which the operation right is granted, are reflected in the image in the window, to which the operation right is not granted. As a result, the synchronous state of images displayed in a plurality of windows of a plurality of viewers in a correspondence relation, respectively, is ensured. Hereinbelow, the window, to which the operation right is granted, is referred to as "presenter window". The window, to which the operation right is not granted, is referred to as "audience window".

The value "1" is set in the asynchronous flag, in a case where the synchronous state of a plurality of windows of a plurality of viewers in a correspondence relation is temporarily canceled and the asynchronous state is established. The asynchronous flag is set based on an asynchronous request from a viewer. The asynchronous flag is reset based on a synchronous return request from a viewer.

The synchronous processing unit 25 refers to the above-mentioned synchronous control table, and performs synchronous processing of images displayed in a plurality of windows of a plurality of viewers in a correspondence relation. Every time an instruction to operate an image in a presenter window is given by a user, the synchronous processing unit 25 is capable of receiving, by using the communication unit 21, a synchronous commission including image location information, a viewer ID, and a window ID of a presenter window sent from a viewer that has the window. In a case of receiving the synchronous commission, the synchronous processing unit 25 sends a synchronous request to the other viewers by using the communication unit 21. The synchronous request includes the above-mentioned respective pieces of information included in the received synchronous commission.

The synchronous processing unit 25 is capable of receiving an operation right acquisition request by using the communication unit 21. When an operation right acquisition button in the audience window is operated, a viewer that has the window sends the operation right acquisition request. The operation right acquisition request includes the viewer ID and the window ID of the audience window. Based on the viewer ID and the window ID included in the received operation right acquisition request, the synchronous processing unit 25 sets an operation right flag with respect to the audience window in the synchronous control table. In addition, the synchronous processing unit 25 resets an operation right flag of a presenter window having the window ID same as the window ID of the audience window. As a result, the operation right is moved between a plurality of windows in a correspondence relation.

The synchronous processing unit 25 is capable of receiving an asynchronous request by using the communication unit 21. When an asynchronous button in an audience window is operated, the asynchronous request is sent from a viewer that has the window. The asynchronous request includes the viewer ID and the window ID of the audience window. Based on the viewer ID and the window ID included in the received asynchronous request, the synchronous processing unit 25 sets an asynchronous flag with respect to the audience window in the synchronous control table. As a result, the audience window is set as the asynchronous state.

The synchronous processing unit 25 is capable of receiving a synchronous return request by using the communication unit 21. When a synchronous button in an audience window set as the asynchronous state is operated, the synchronous return request is sent from a viewer that has the window. The synchronous return request includes the viewer ID and the window ID of the audience window. Based on the viewer ID and the window ID included in the received synchronous return request, the synchronous processing unit 25 resets the asynchronous flag with respect to the audience window in the synchronous control table.

The information processing system 100 of this embodiment employs a server/client system. Therefore, the synchronous server 20 performs the synchronous processing. However, the present disclosure essentially has no relation to a server/client system. In a case of employing a peer-to-peer system, at least one of the plurality of viewers 30A, 30B may perform the synchronous processing that the synchronous server 20 performs.

[Viewers 30A, 30B]

Each of the viewers 30A, 30B may be configured by, for example, a general computer system.

Figure 6:
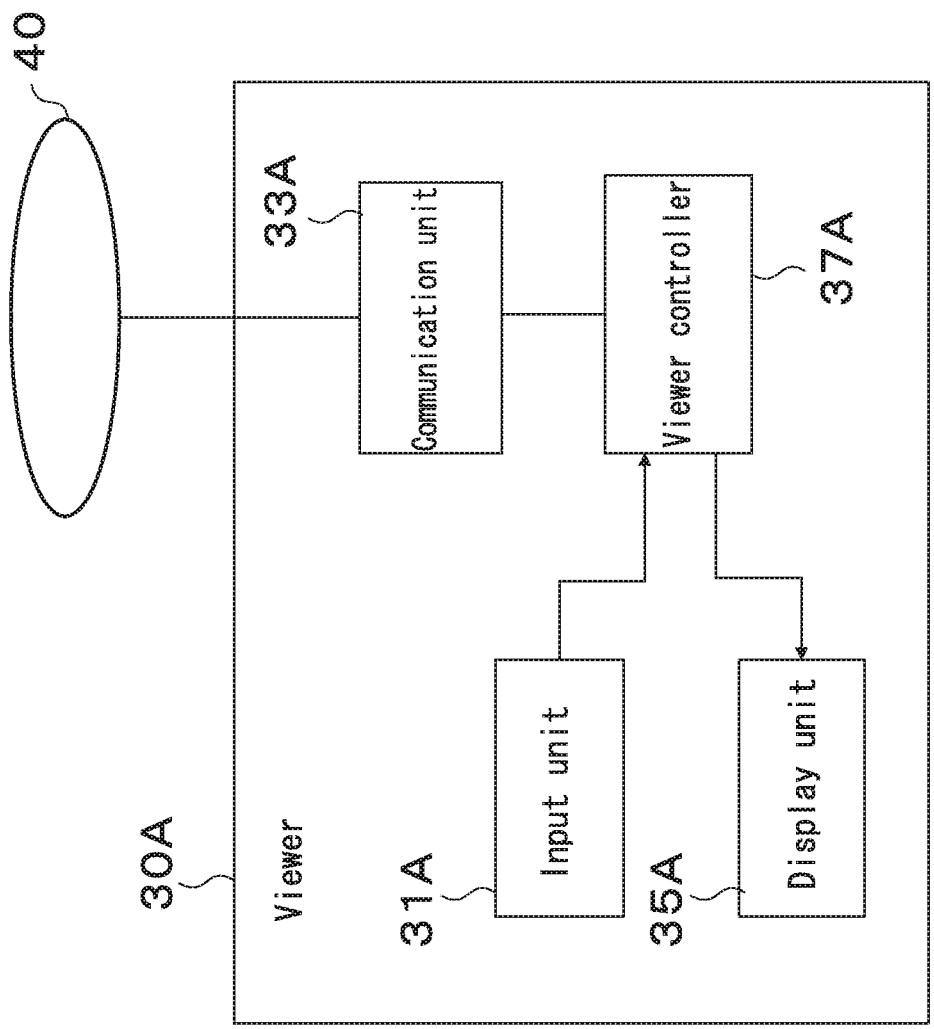
FIG. 6 is a block diagram showing the functional structure of the viewer of FIG. 1.

FIG. 6 is a block diagram showing a functional structure of each of the viewers 30A, 30B implemented by a general computer system. Note that, because the configurations of the two viewers 30A, 30B are the same, the configuration of the first viewer 30A will only be described.

As shown in FIG. 6, the first viewer 30A includes an input unit 31A, a communication unit 33A, a display unit 35A, a viewer controller 37A, and the like.

The input unit 31A such as, for example, a mouse, a keyboard, a touchpad, a sound input unit, or the like receives inputs from a user. By using the input unit 31A, a user is capable of inputting instructions to perform various requests. The various requests includes an instruction of various operations with respect to an image in a window, the operation right acquisition request, the asynchronous request, the synchronous return request, an inter-window copy request, and the like.

The communication unit 33A sends various requests such as the image data request, the synchronous commission, the operation right acquisition request, the asynchronous request, the synchronous return request, and the like to the synchronous server 20 via the network 40. The communication unit 33A receives replies to the respective requests from the synchronous server 20 via the network 40.

The display unit 35A is a device that optically outputs images such as, for example, a cathode-ray tube (CRT), a plasma display, a liquid crystal display, an organic EL (electroluminescence) display, or the like.

Based on operation information, the viewer controller 37A (controller) calculates image location information necessary to update an image in a window. The operation information is input by a user by using the input unit 31A in order to update the image in the presenter window. The viewer controller 37A sends an image data request to the image server 10 by using the communication unit 33A. The image data request includes the image location information, the viewer ID, and the window ID of the presenter window. Further, the viewer controller 37A sends a synchronous commission to the synchronous server 20 by using the communication unit 33A. The synchronous commission includes the image location information, the viewer ID, and the window ID of the presenter window.

Except the case where an asynchronous state is set in the audience window, the viewer controller 37A disables operation information input by a user by using the input unit 31A. The operation information is input to update an image in the audience window. As a result, it is possible to avoid a breakdown of the synchronous relation between the presenter and the audience.

The viewer controller 37A updates the image in the window based on the image data, which is replied from the image server 10 in response to the sent image data request. Further, in a case where the viewer controller 37A receives a synchronous request including image location information from the synchronous server 20, the viewer controller 37A sends an image data request to the image server 10 via the communication unit 33A. The image data request includes the image location information included in the synchronous request. The viewer controller 37A updates the image in the window based on the image data replied from the image server 10.

Similar to the first viewer 30A, the second viewer 30B includes an input unit 31B, a communication unit 33B, a display unit 35B, a viewer controller 37B, and the like, too. The description thereof will be omitted to avoid overlap.

[GUI in Relation to Window]

Next, GUIs (Graphical User Interfaces) in relation to the windows will be described.

Figure 12:
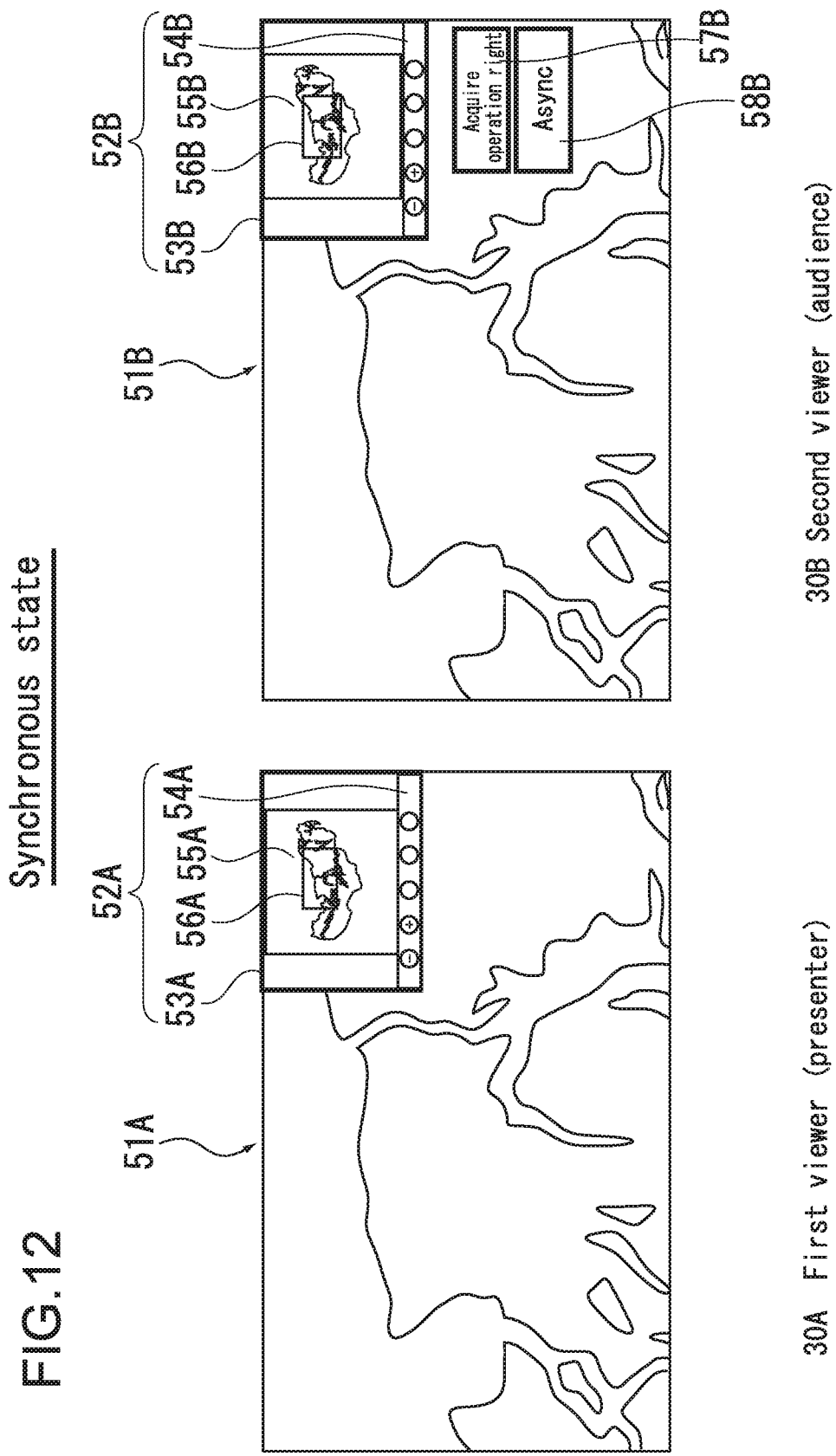
FIG. 12 is a diagram showing examples of windows displayed in the respective viewers in the single-window display mode.

FIG. 12 is a diagram showing examples of the two windows of the two viewers 30A, 30B in the synchronous state. The left side in FIG. 12 shows a first window 51A of the first viewer 30A set as the presenter. The right side shows a second window 51B of the second viewer 30B set as the audience.

Each of the first window 51A and the second window 51B includes an image operation GUI 52A, 52B to receive instructions from a user to operate the image in the window. The image operation GUI 52A, 52B includes a thumbnail map 53A, 53B and a thumbnail map operation GUI 54A, 54B. The thumbnail map 53A, 53B includes a zoom-out image 55A, 55B of the entire object and a frame 56A, 56B. The frame 56A, 56B equivalently shows the image area, which is displayed in the first window 51A or the second window 51B, in the zoom-out image 55A, 55B. Based on instructions from a user, the frame 56A, 56B may move in the zoom-out image 55A, 55B, in an arbitrary direction and for an arbitrary distance. Based on operation information of the move of the frame 56A, 56B, the viewer controller 37A calculates image location information. Meanwhile, the thumbnail map operation GUI 54A, 54B includes GUI components such as a plurality of buttons and the like. The plurality of buttons receive instructions from a user to operate an image such as moves, zoom factor changes, rotations, and the like with respect to the image. Note that, in the thumbnail map 53A, 53B, move operations of the frame 56A, 56B may be performed by drag operations and the like by using a mouse and the like. The image operation GUIs 52A, 52B to operate the image have been described above.

Further, an operation right acquisition button 57B and an asynchronous/synchronous change button 58B are displayed in the audience window, for example, in the second window 51B.

The operation right acquisition button 57B is a button in the audience second window 51B, which is used in a case where a user wishes to acquire the operation right. In a case where the operation right acquisition button 57B is operated, the operation right is granted. Then, the operation right acquisition button 57B disappears from the second window 51B. In a case where the operation right acquisition button 57B disappears from the second window 51B, a user recognizes that the operation right is granted to his window, and that his window functions as a presenter. Then, the user may start image operations.

The asynchronous/synchronous change button 58B is a button, which is used in a case where a user wishes to use the audience second window 51B personally, in a temporary asynchronous state with respect to the presenter first window 51A. In a case where the asynchronous/synchronous change button 58B is operated and the temporary asynchronous state starts, the asynchronous/synchronous change button 58B changes from "Async" to "Sync". In this state, operations of the image in the second window 51B are allowed through inputs in the image operation GUI 52B. When "Sync" is displayed, the asynchronous/synchronous change button 58B functions as a button to return from the asynchronous state to the synchronous state.

Further, when the audience second window 51B and the presenter first window 51A are in the synchronous state, a user starts any input operation in the image operation GUI 52B of the second window 51B by using the input unit 31B. In this case, also, the audience second window 51B changes from the synchronous state to the asynchronous state. In this case, also, the asynchronous/synchronous change button 58B changes from "Sync" to "Async". Further, in the case where an input operation in the image operation GUI 52B changes the synchronous/asynchronous state, the first input operation in the image operation GUI 52B functions as the actual operation in the image in the second window 51B. As a result, a user may start to operate the image personally more promptly than the case where the asynchronous/synchronous change button 58B is operated.

Note that, in the present disclosure, means for inputting instructions by a user to operate an image may not be limited to the image operation GUI 52B. For example, a pointer cursor may be directly displayed in the image in the second window 51B, and the image may be operated through input operations (click, double click, right click, left click, drag, and the like) by using the pointer cursor. In this case, similarly, the first input operation may function as the actual operation in the image in the second window 51B.

[Operations of Information Processing System 100]

Next, operations of the information processing system 100 of this embodiment will be described.

The description will be made in the following order.

1. Synchronous processing in the single-window display mode, and synchronous/asynchronous change processing 2. Operation right move processing in the single-window display mode 3. Synchronous processing in the multi-window display mode

[1. Synchronous Processing in Single-Window Display Mode, and Synchronous/Asynchronous Change Processing]

Figure 7:
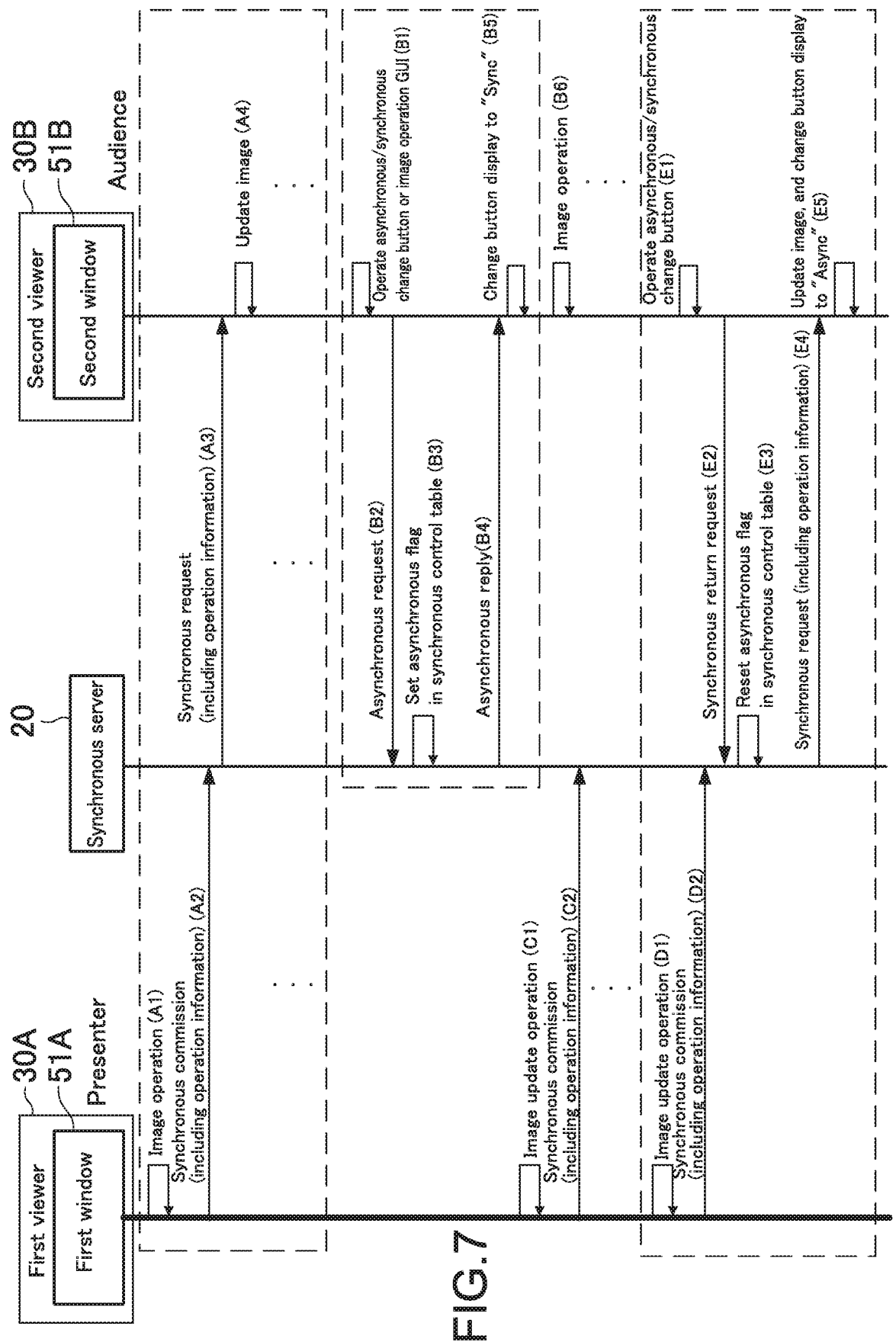
FIG. 7 is a sequence diagram showing the flow of the synchronous processing including synchronous/asynchronous change operations between the viewers.

Next, with reference to FIG. 7 and FIG. 12 to FIG. 17, the synchronous processing operations in the single-window display mode will be described. FIG. 7 is a sequence diagram showing the synchronous processing flow including the synchronous/asynchronous change operations. FIG. 12 to FIG. 17 are diagrams showing display examples in the two windows in a correspondence relation, in the single-window display mode.

The left side in FIG. 12 shows the presenter first window 51A of the first viewer 30A, and the right side in FIG. 12 shows the audience second window 51B of the second viewer 30B. The first window 51A and the second window 51B are in the synchronous state. The same images are thus displayed in the first window 51A and the second window 51B. Further, the operation right acquisition button 57B and the asynchronous/synchronous change button 58B are displayed in the audience second window 51B. "Async" is displayed in the asynchronous/synchronous change button 58B.

In the first viewer 30A, a user inputs an arbitrary operation in the image displayed in the presenter first window 51A (A1 in FIG. 7). Based on the operation information input by the user by using the input unit 31A, the viewer controller 37A of the first viewer 30A calculates image location information. Based on the image location information, the viewer controller 37A performs controls to update the image in the first window 51A. In addition, the viewer controller 37A performs controls to send a synchronous commission including the image location information to the synchronous server 20 by using the communication unit 33A (A2 in FIG. 7).

Receiving the synchronous commission, the synchronous server 20 extracts the image location information from the synchronous commission, creates a synchronous request including the image location information, and sends the synchronous request to the second viewer 30B (A3 in FIG. 7).

The viewer controller 37B of the second viewer 30B receives the synchronous request by using the communication unit 33A. Then, the viewer controller 37B controls to extract the image location information from the synchronous request, and to update the image in the second window 51B based on the image location information (A4 in FIG. 7).

The above-mentioned operations are repeated, as long as the first viewer 30A holds the operation right, every time an image operation is input in the first window 51A of the first viewer 30A.

Figure 13:
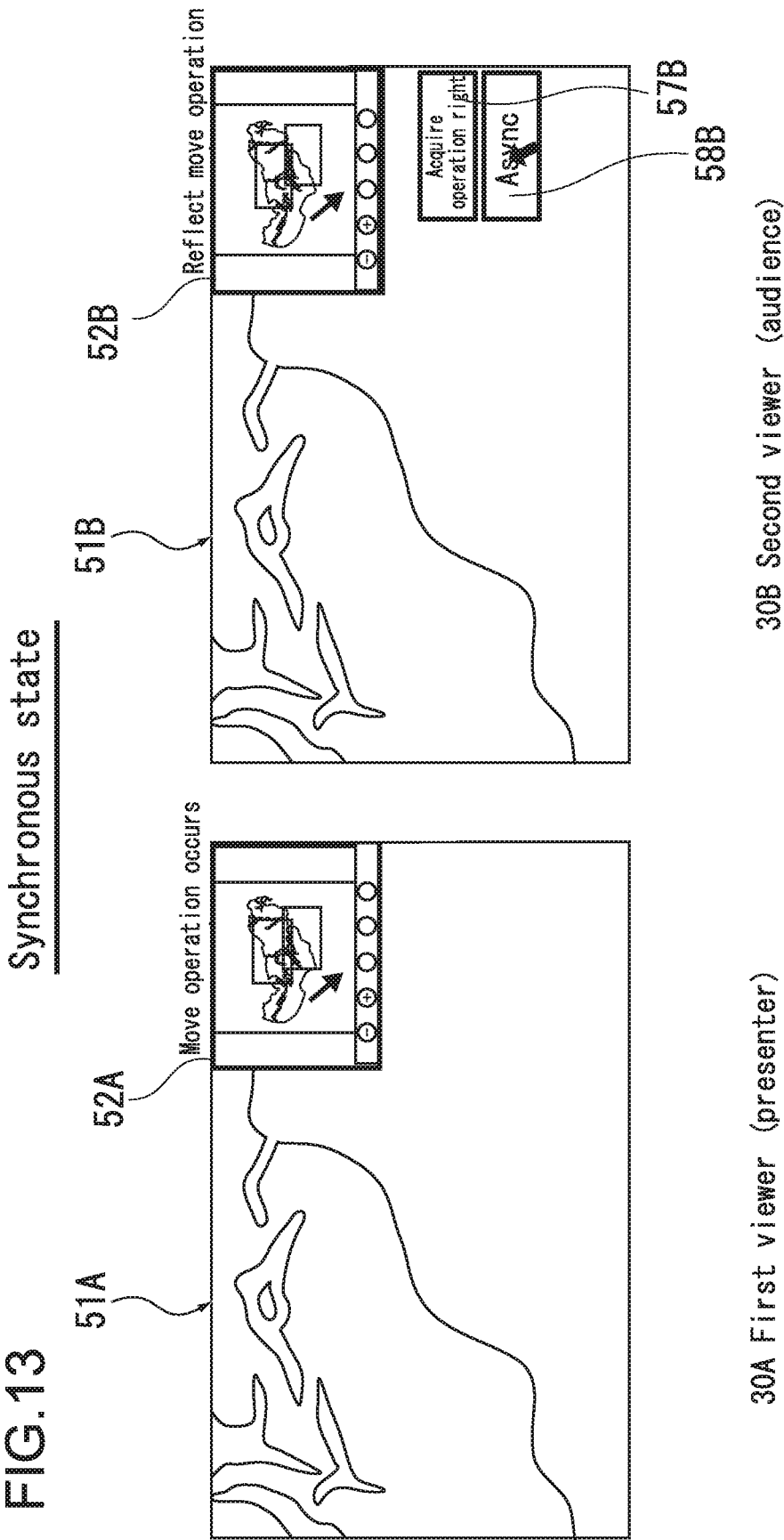
FIG. 13 is a diagram showing the state where an asynchronous button is operated with respect to an image in a first window being a presenter.

For example, as shown in FIG. 13, in a case where a move operation is input with respect to the image in the first window 51A as the presenter, the operation is reflected in the image in the second window 51B as the audience.

As shown in FIG. 12 and FIG. 13, the operation right acquisition button 57B and the asynchronous/synchronous change button 58B are displayed in the the audience second window 51B. Here, operations in a case where a user operates the asynchronous/synchronous change button 58B or the image operation GUI 52B in the audience second window will be described.

In a case where a user operates the asynchronous/synchronous change button 58B or the image operation GUI 52B in the audience second window (B1 in FIG. 7), the viewer controller 37B of the second viewer 30B sends an asynchronous request including the viewer ID and the window ID to the synchronous server 20 (B2 in FIG. 7).

Receiving the asynchronous request, the synchronous processing unit 25 of the synchronous server 20 sets the asynchronous flag of the second window 51B in the synchronous control table (B3 in FIG. 7). As a result, the synchronous state of the first window 51A and the second window 51B is canceled. After that, the synchronous processing unit 25 returns an asynchronous reply to the second viewer 30B (B4 in FIG. 7). Receiving the asynchronous reply, the viewer controller 37B of the second viewer 30B changes the asynchronous/synchronous change button 58B in the second window 51B to "Sync". In addition, the viewer controller 37B sets the asynchronous state, which allows a user to input operations in the image operation GUI 52B to operate the image in the second window 51B (B5 in FIG. 7).

After that, until the synchronous processing unit 25 of the synchronous server 20 receives a synchronous return request from the second viewer 30B, the synchronous processing unit 25 prohibits the transmission of image location information from the first viewer 30A to the second viewer 30B. As a result, a user of the second viewer 30B may operate the image in the second window 51B of the second viewer 30B personally, and the user may input arbitrary operations.

Figure 14:
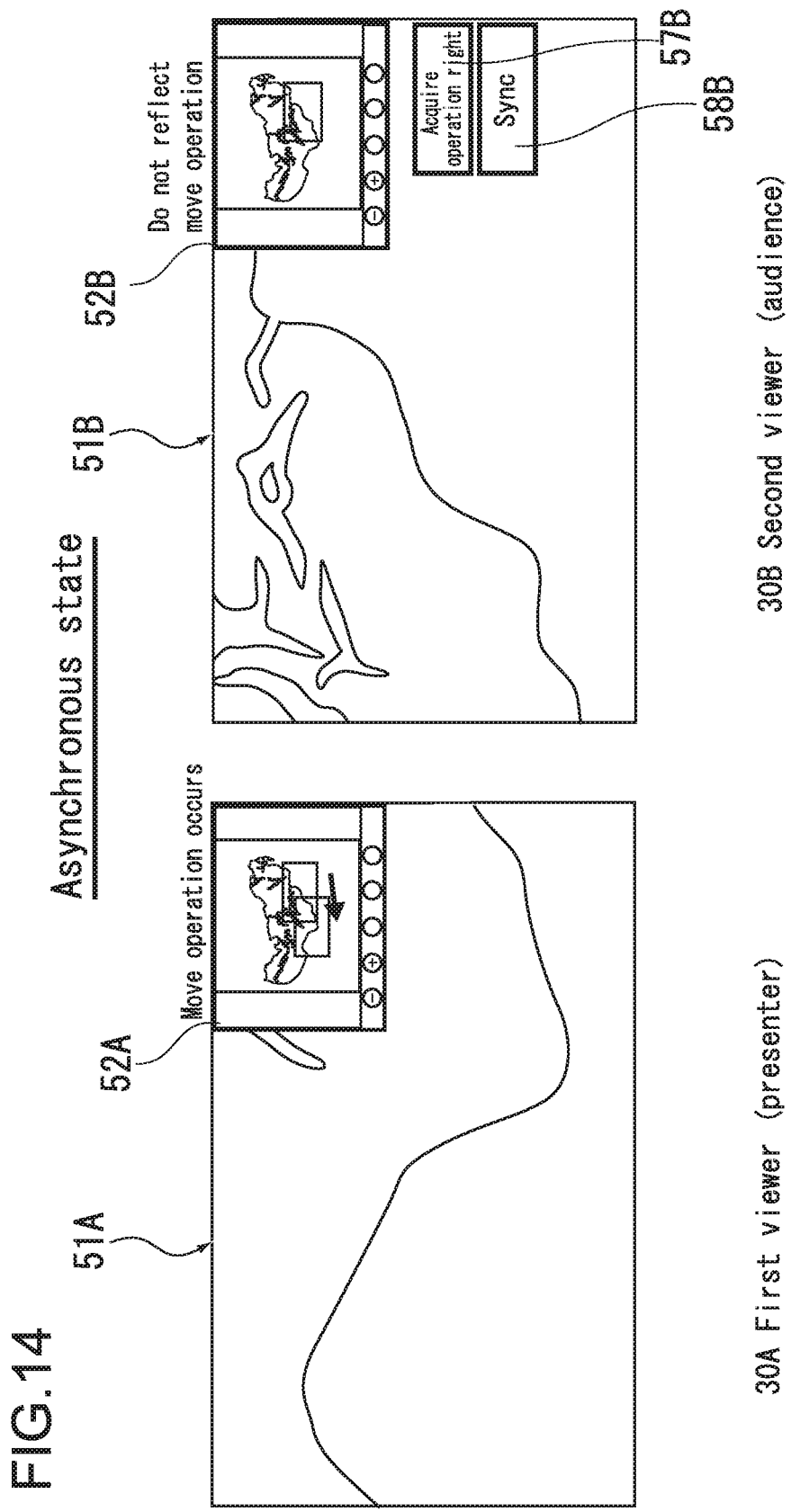
FIG. 14 is a diagram showing the state where a moving operation is performed with respect to the image displayed in the presenter first window.
Figure 15:
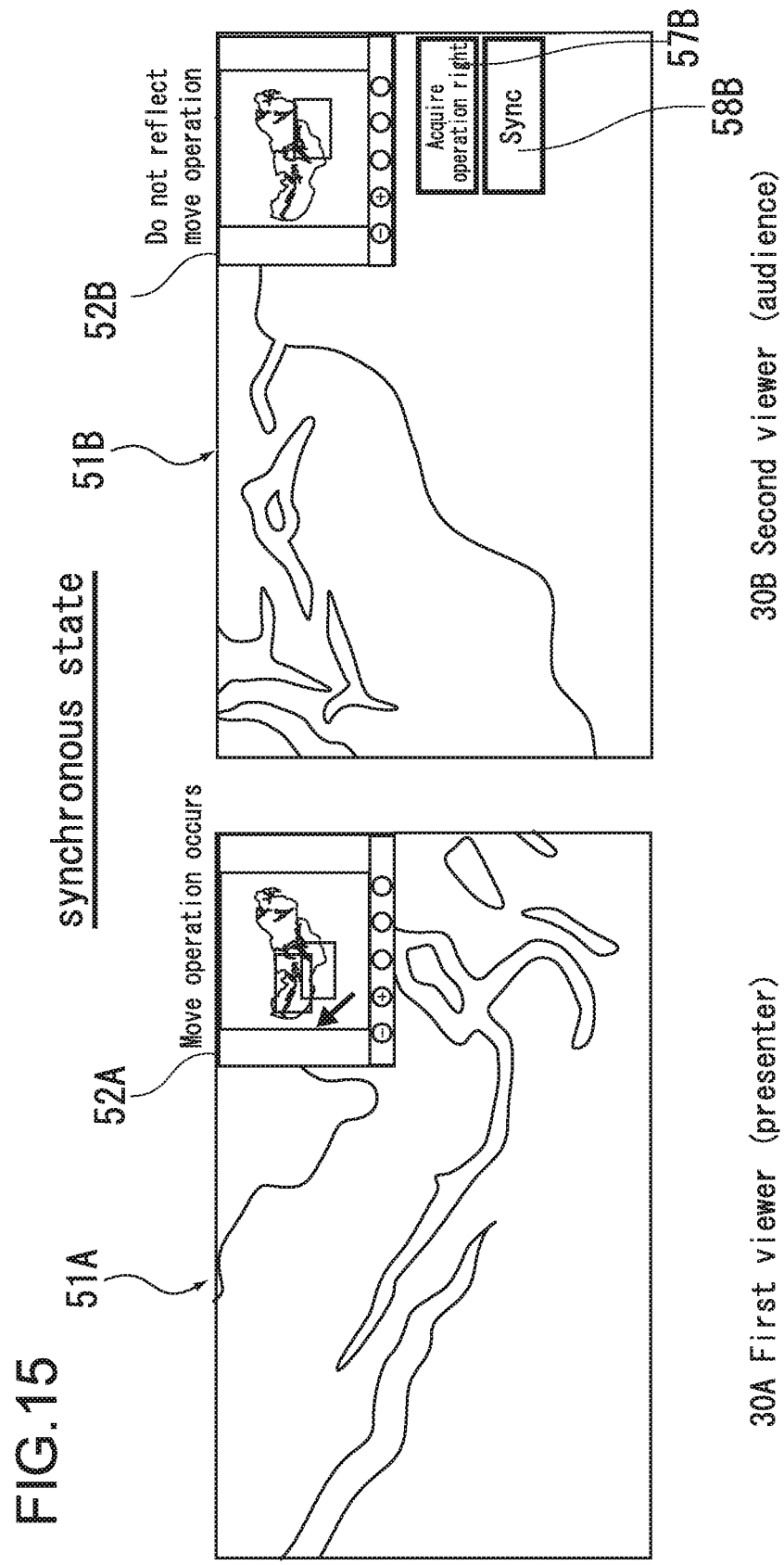
FIG. 15 is a diagram showing the state where the moving operation is continuously performed with respect to the image displayed in the presenter first window.

For example, in FIG. 13, the asynchronous/synchronous change button 58B or the image operation GUI 52B in the audience second window 51B is operated. As a result, the asynchronous state of the second window 51B and the presenter first window 51A is established, and the asynchronous/synchronous change button 58B changes from "Async" to "Sync". After that, as shown in FIG. 14 and FIG. 15, in a case where the image displayed in the presenter first window 51A is operated (C1 in FIG. 7), a synchronous request including image location information based on the operation information is not given to the second viewer 30B. Therefore, the operation is not reflected in the image in the second window 51B. Note that FIG. 14 and FIG. 15 show a case where operations on the image displayed in the presenter first window 51A are repeated, and, meanwhile, a user does not input operations in the image in the audience second window 51B.

Figure 16:
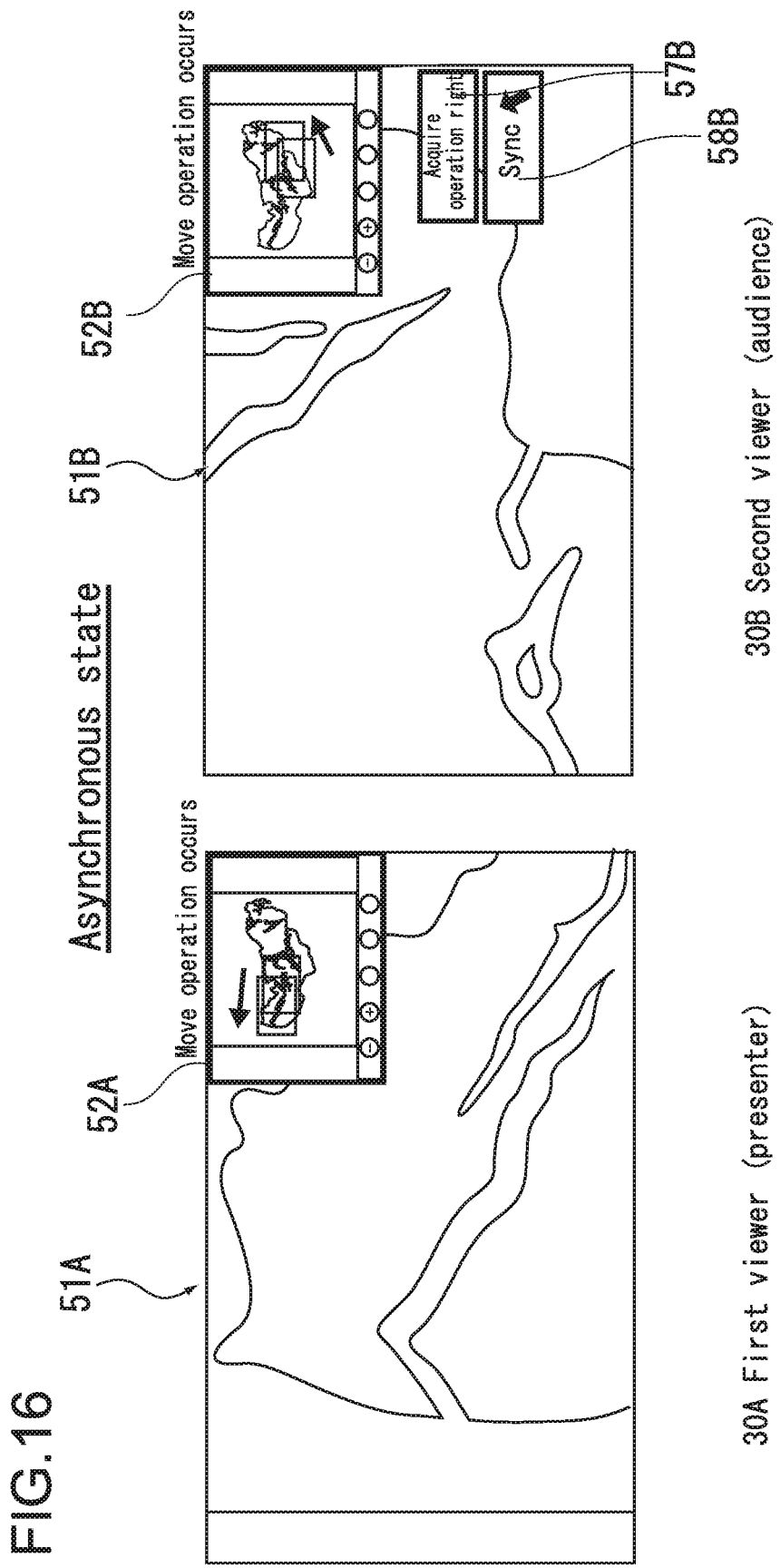
FIG. 16 is a diagram showing the state where the moving operation is performed with respect to the image displayed in an audience second window.

Then, as shown in FIG. 16, in a case where a user inputs operation information in the image displayed in the audience second window 51B by using the input unit 31A, the image in the audience second window 51B is updated based on the operation information (B6 in FIG. 7).

As described above, it is possible to establish the asynchronous state of the image in the audience second window 51B and the image in the presenter first window 51A. Therefore, a user may operate the image in the audience second window 51B at will.

Note that, the audience second window 51B changes to the asynchronous state based on operations of the image operation GUI 52B. In this case, based on the first operation in the image operation GUI 52B, the image displayed in the second window 51B is actually operated.

Next, in FIG. 16, a case where the asynchronous/synchronous change button 58B displayed as "Sync" is operated (E1 in FIG. 7) will be described. In this case, the viewer controller 37B of the second viewer 30B sends a synchronous return request to the synchronous server 20 by using the communication unit 33A (E2 in FIG. 7). The synchronous return request includes the viewer ID and the window ID of the audience second window 51B.

Receiving the synchronous return request, the synchronous processing unit 25 of the synchronous server 20 resets the asynchronous flag of the second window 51B in the synchronous control table based on the viewer ID and the window ID included in the synchronous return request (E3 in FIG. 7). Further, the synchronous processing unit 25 sends a synchronous request to the second viewer 30B that sent the synchronous return request (E4 in FIG. 7). The synchronous request includes the latest image location information. The latest image location information is calculated based on the latest operation (D1 in FIG. 7) on the image in the second window 51B as the presenter.

Figure 17:
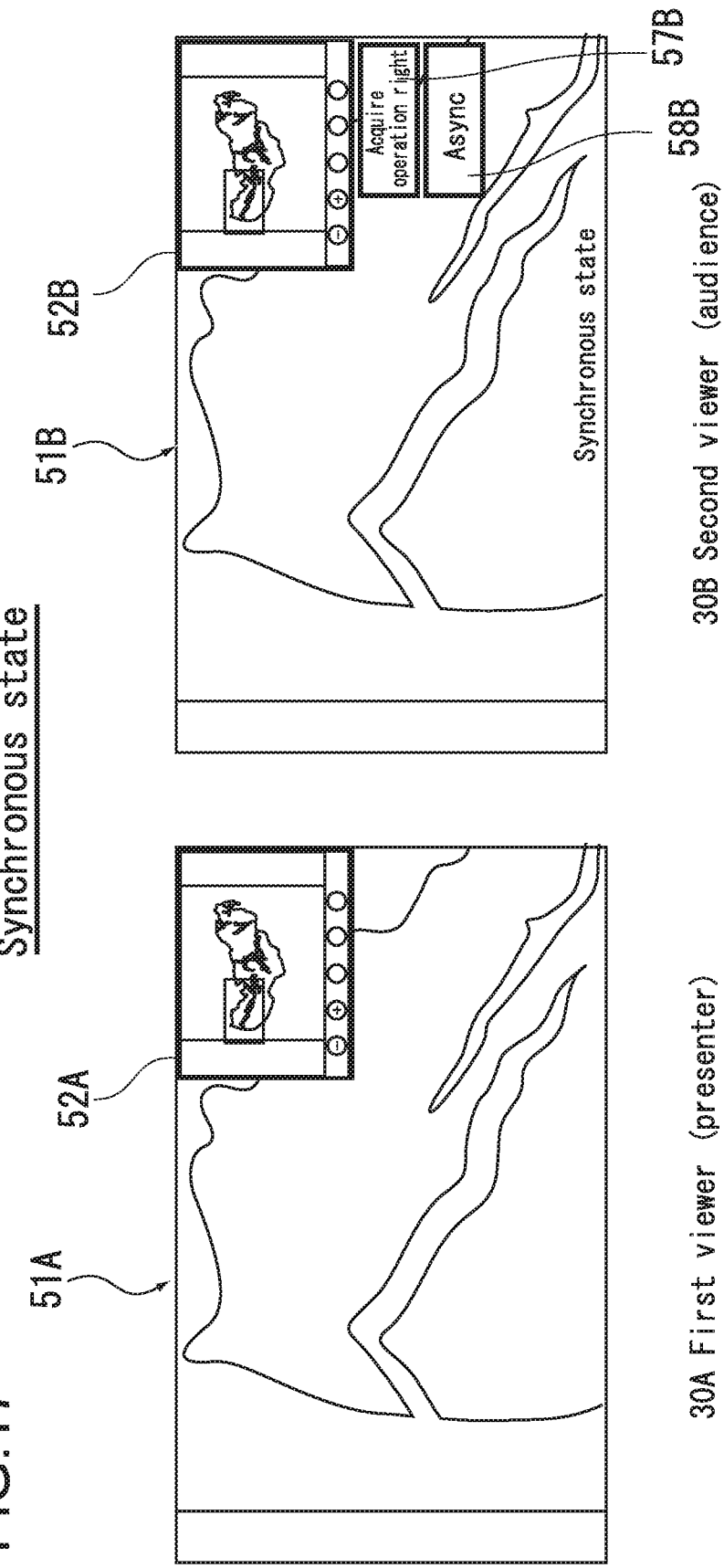
FIG. 17 is a diagram showing the state where the synchronous relation between the first window and the second window is re-established.

Receiving the synchronous request, the viewer controller 37B of the second viewer 30B controls to update the image in the second window 51B based on the image location information included in the received synchronous request. In addition, the viewer controller 37B changes the asynchronous/synchronous change button 58B from "Sync" to "Async" (E5 in FIG. 7). As a result, as shown in FIG. 17, the synchronous state of the first window 51A and the second window 51B is re-established.

[2. Operation Right Move Processing in Single-Window Display Mode]

Figure 8:
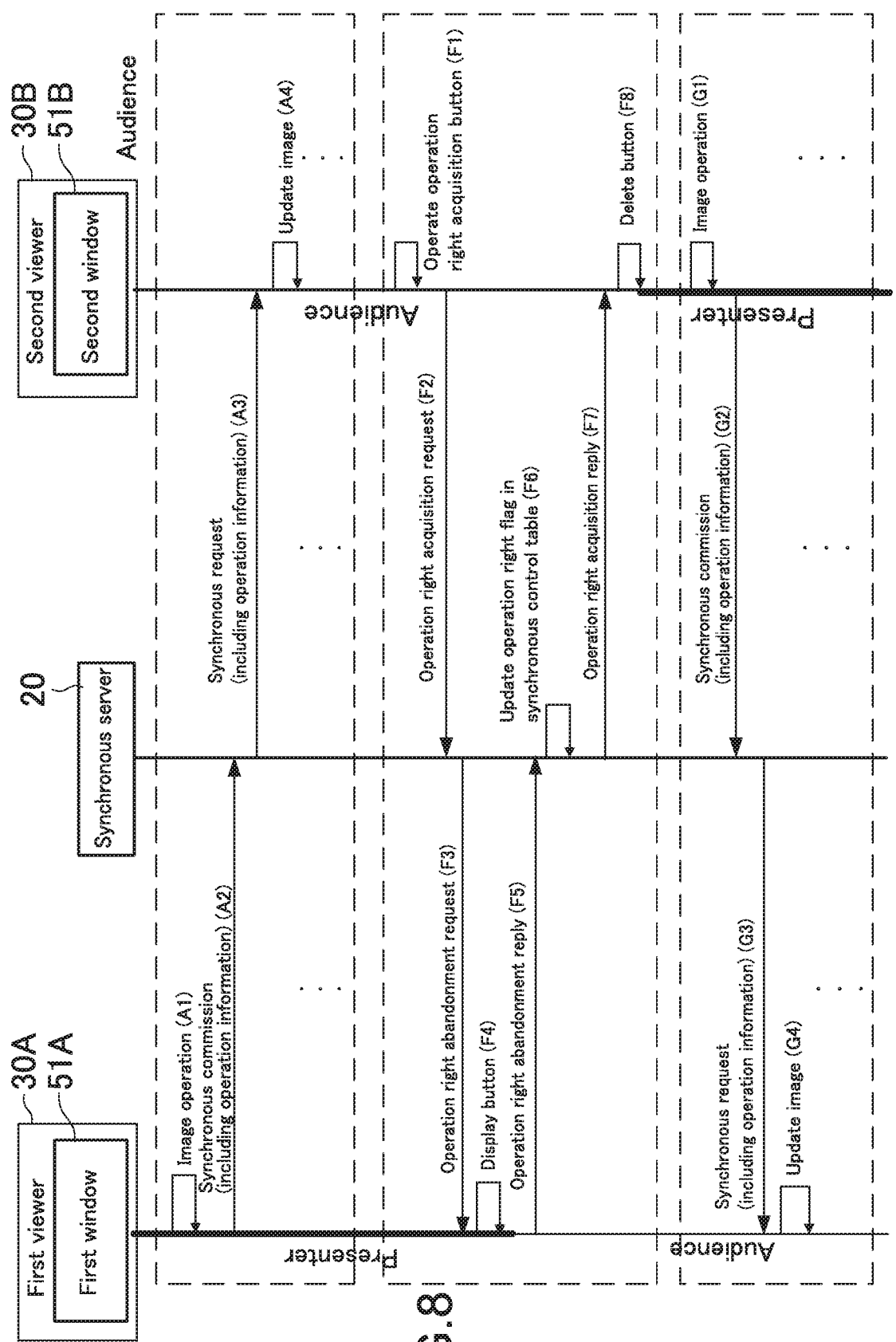
FIG. 8 is a sequence diagram showing the flow of the synchronous processing including operation right move processing between the viewers.
Figure 18:
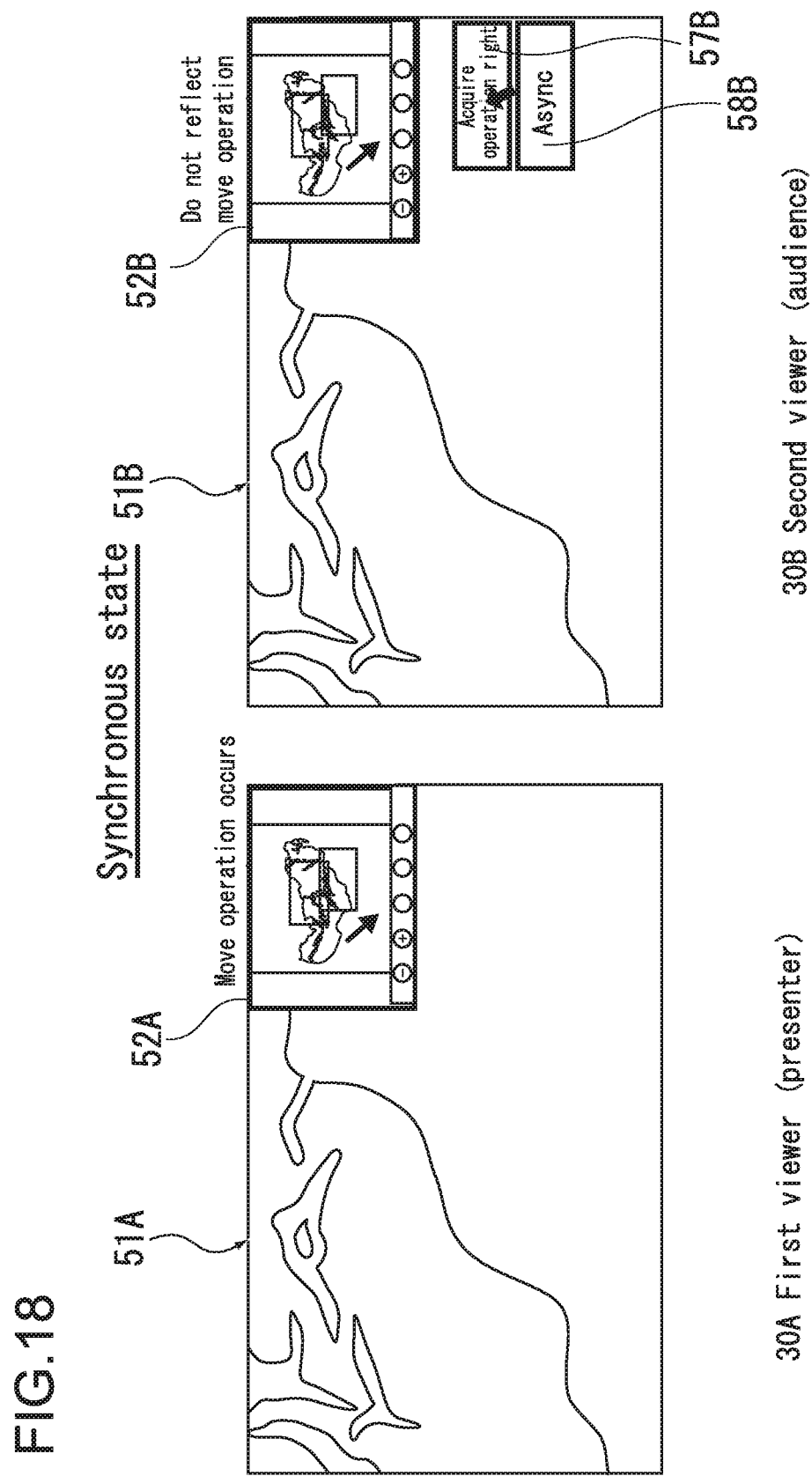
FIG. 18 is a diagram showing window display examples showing operation right move processing between the viewers.
Figure 19:
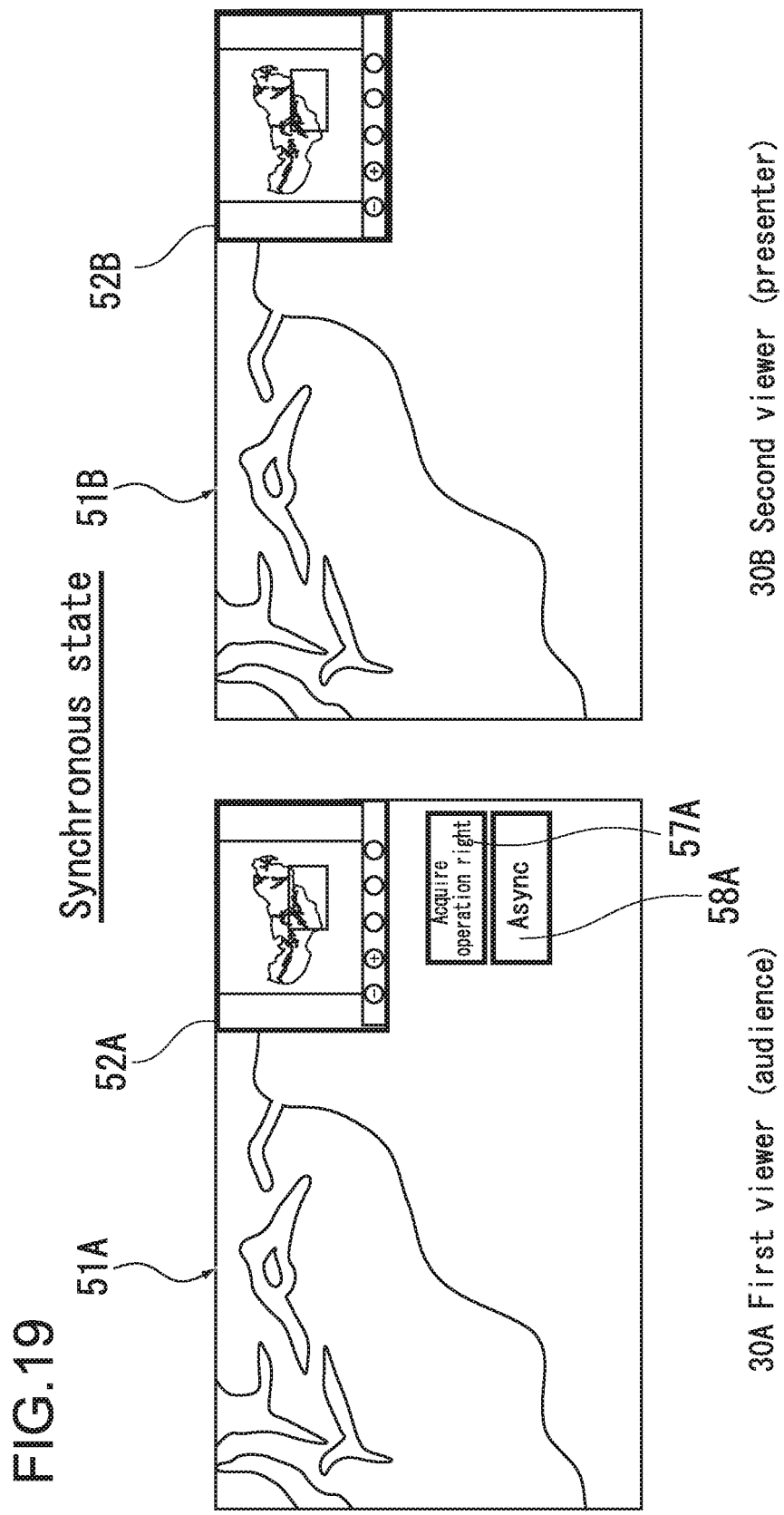
FIG. 19 is a diagram similarly showing window display examples showing the operation right move processing between the viewers.

Next, with reference to FIG. 8, FIG. 18, and FIG. 19, the operation right move processing in the single-window display mode will be described. FIG. 8 is a sequence diagram showing the flow of synchronous processing including operation right move processing between the viewers. FIG. 18 and FIG. 19 are diagrams showing display examples of the windows in the operation right move processing.

In A1 to A4 in FIG. 8, operations are input in the image displayed in the presenter first window 51A by a user. The operations are reflected in the image displayed in the audience second window 51B. The behaviors in A1 to A4 in FIG. 8 are the same as the behaviors A1 to A4 in FIG. 7.

As shown in FIG. 18, a user operates the operation right acquisition button 57B in the audience second window 51B (F1 in FIG. 8). In this case, the viewer controller 37B of the second viewer 30B sends an operation right acquisition request to the synchronous server 20 (F2 in FIG. 8). The operation right acquisition request includes the viewer ID and the window ID of the audience second window 51B.

Receiving the operation right acquisition request, the synchronous processing unit 25 of the synchronous server 20 creates an operation right abandonment request. The operation right abandonment request includes the viewer ID and the window ID extracted from the operation right acquisition request. The synchronous processing unit 25 sends the operation right abandonment request to the first viewer 30A (F3 in FIG. 8).

Receiving the operation right abandonment request, as shown in FIG. 19, the viewer controller 37A of the first viewer 30A controls to display an operation right acquisition button 57A and an asynchronous/synchronous change button 58A in the first window 51A (F4 in FIG. 8). The viewer controller 37A returns an operation right abandonment reply to the synchronous server 20 (F5 in FIG. 8).

Receiving the operation right abandonment reply from the first viewer 30A, the synchronous server 20 resets the operation right flag of the first window 51A in the synchronous control table. In addition, the synchronous server 20 sets the operation right flag of the second window 51B (F6 in FIG. 8). After that, the synchronous processing unit 25 of the synchronous server 20 sends an operation right acquisition reply to the second viewer 30B (F7 in FIG. 8). The operation right acquisition reply at least includes the window ID of the second window 51B.

Receiving the operation right acquisition reply, as shown in FIG. 19, the second viewer 30B deletes the operation right acquisition button 57B and the asynchronous/synchronous change button 58B from the second window 51B (F8 in FIG. 8).

Accordingly, the operation right is moved from the first window 51A to the second window 51B. After that, a user inputs operations in the image displayed in the first window 51A as the present presenter. The operations are reflected in the image displayed in the second window 51B as the present audience (G1 to G4 in FIG. 8).

[3. Synchronous Processing in Multi-Window Display Mode]

Next, the synchronous processing in the multi-window display mode will be described.

In a case where a plurality of windows are displayed in each viewer (multi-window display mode), there are a plurality of combinations of windows in the correspondence relation. Therefore, the operation right is granted to one window for each combination of windows in the correspondence relation.

Figure 20:
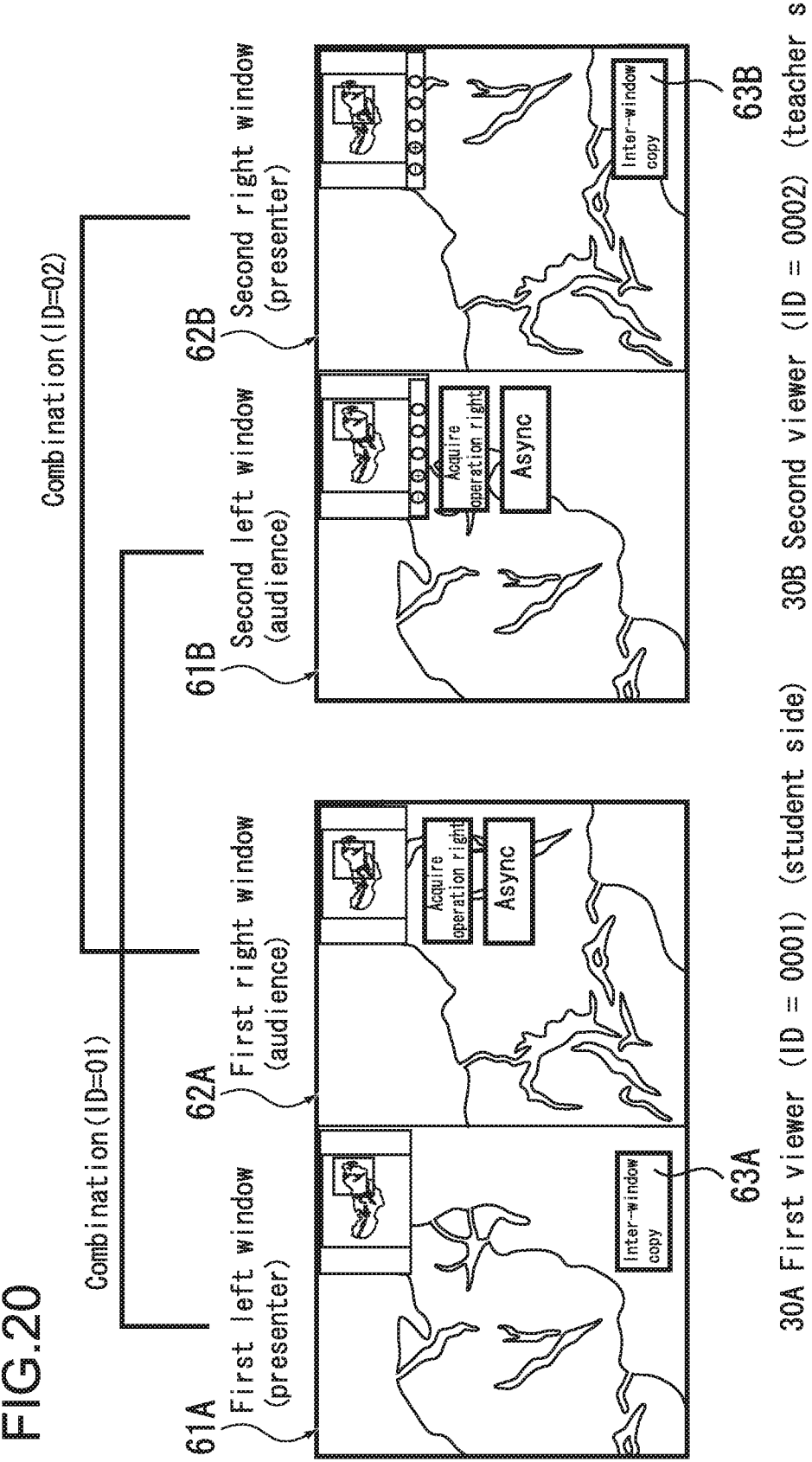
FIG. 20 is a diagram showing display examples in the multi-window display mode.

FIG. 20 is a diagram showing a multi-window display example corresponding to the synchronous control table of FIG. 4. In this example, there are the first viewer 30A having a viewer ID "0001", and the second viewer 30B having a viewer ID "0002". The first viewer 30A includes a first left window 61A having a window ID="01", and a first right window 62A having a window ID="02". The second viewer 30B includes a second left window 61B having a window ID="01", and a second right window 62B having a window ID="02". Further, in the window combination of the window ID=01, the first left window 61A holds the operation right. In the window combination of the window ID=02, the second right window 62B holds the operation right.

In the synchronous processing, the synchronous/asynchronous change processing, and the operation right move processing in the multi-window display mode, behaviors similar to the behaviors in the single-window display mode are independently performed in the unit of the window combination in the correspondence relation. So, the processing in the multi-window display mode is not different from the processing in the single-window display mode. Therefore, description thereof will be omitted.

One of the effective uses of the multi-window display mode may be an educational system. In an educational system, there are two window combinations in the correspondence relation. In this situation, the operation right to one combination is granted to the teacher-side viewer. The operation right to the other combination is granted to the student-side viewer. The teacher operates the image displayed in the window, the operation right to which is granted to the teacher-side viewer. The student may view the image operated by the teacher by using the student-side viewer. Meanwhile, the window, the operation right to which is granted to the student-side viewer, is used in relation to the image displayed in the window, the operation right to which is granted to the teacher-side viewer. For example, the student uses the window, the operation right to which is granted to the student-side viewer, to confirm the area in the vicinity of the image displayed in the window, the operation right to which is granted to the teacher-side viewer, and the details of the image by changing the zoom factor. However, in this case, firstly, it is necessary for the student, by himself, to manually adjust the image position in the window, the operation right to which is granted to the student-side viewer, to the image position displayed in the window, the operation right to which is granted to the teacher-side viewer. Such an adjusting operation may lay a heavy burden on a user.

To the contrary, in the two windows displayed in the multi-window display mode of the information processing system 100 of this embodiment, based on an instruction by a user, the image in the presenter window may be replaced with the copy of the image in the audience window as it is. As a result, it is not necessary to manually adjust the image position in the window, the operation right to which is granted to the student-side viewer, to the image position in the window, the operation right to which is granted to the teacher-side viewer. It is possible to smoothly start the operations to confirm the area in the vicinity of the image displayed in the window, the operation right to which is granted to the teacher-side viewer, and the details of the image.

Next, with reference to FIG. 9 and FIG. 20 to FIG. 25, the synchronous processing in the multi-window display mode including the above-mentioned inter-window image copying will be described.

In FIG. 20, the first viewer 30A (ID=0001) is a student's viewer, and the second viewer 30B (ID=0002) is a teacher's viewer. In the window combination of the window ID=01, the first left window 61A, that is, the student side, holds the operation right. In the window combination of the window ID=02, the second right window 62B, that is, the teacher side, holds the operation right.

Inter-window copy buttons 63A, 63B are displayed in the presenter windows that hold the operation rights (first left window 61A, second right window 62B). The inter-window copy buttons 63A, 63B receive instructions by users to copy images between the above-mentioned windows.

Figure 9:
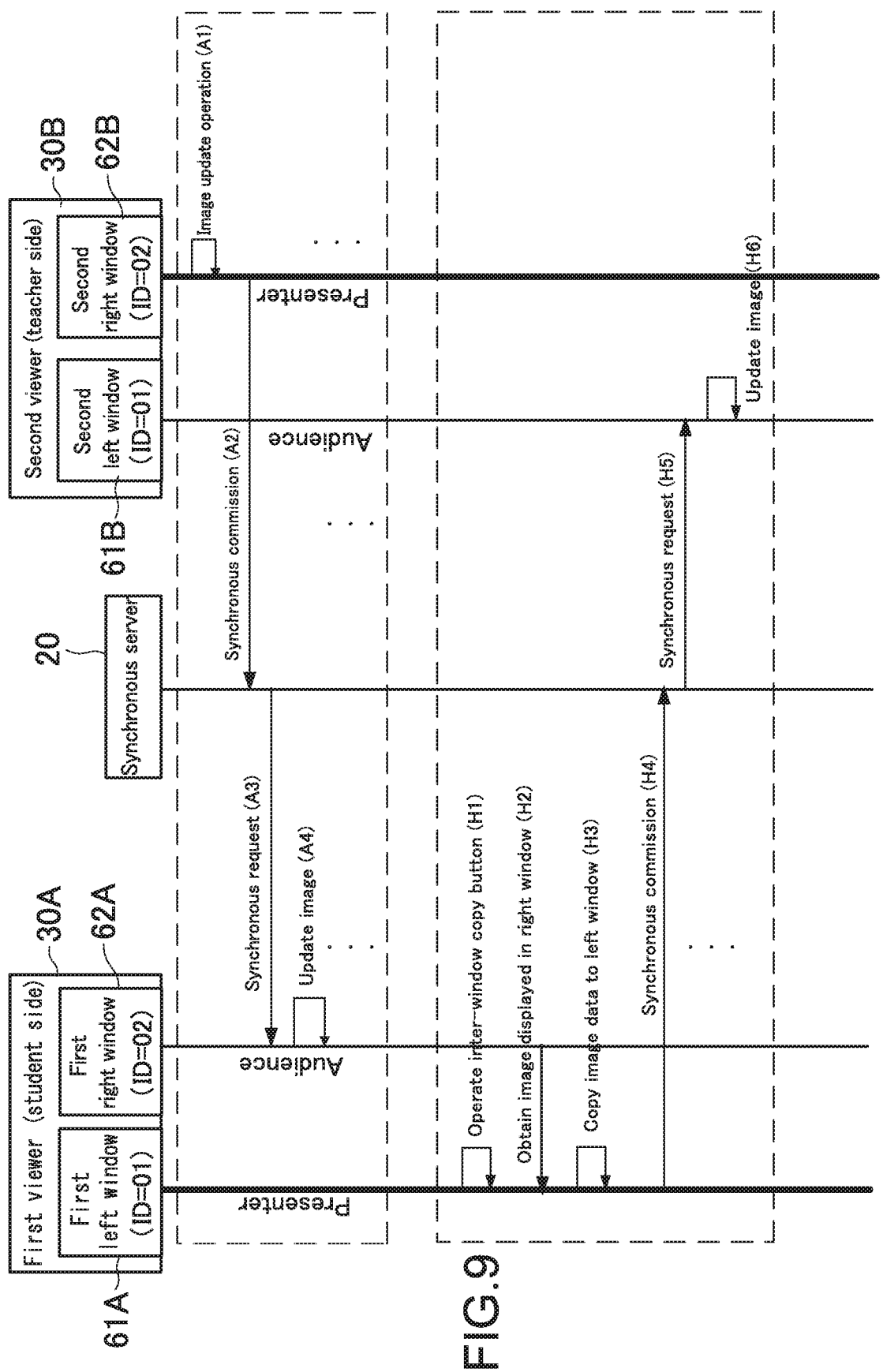
FIG. 9 is a sequence diagram showing the flow of the synchronous processing in the multi-window display mode including inter-window image copying.

FIG. 9 is a sequence diagram showing the flow of synchronous processing in the multi-window display mode including the inter-window image copying.

Here, in A1 to A4 in FIG. 9, operations are input in the image displayed in the second right window 62B (presenter) of the second viewer 30B by a user. The operations are reflected in the image displayed in the first right window 62A (audience) of the first viewer 30A. The behaviors in A1 to A4 in FIG. 9 are the same as the behaviors A1 to A4 in FIG. 7.

Figure 21:
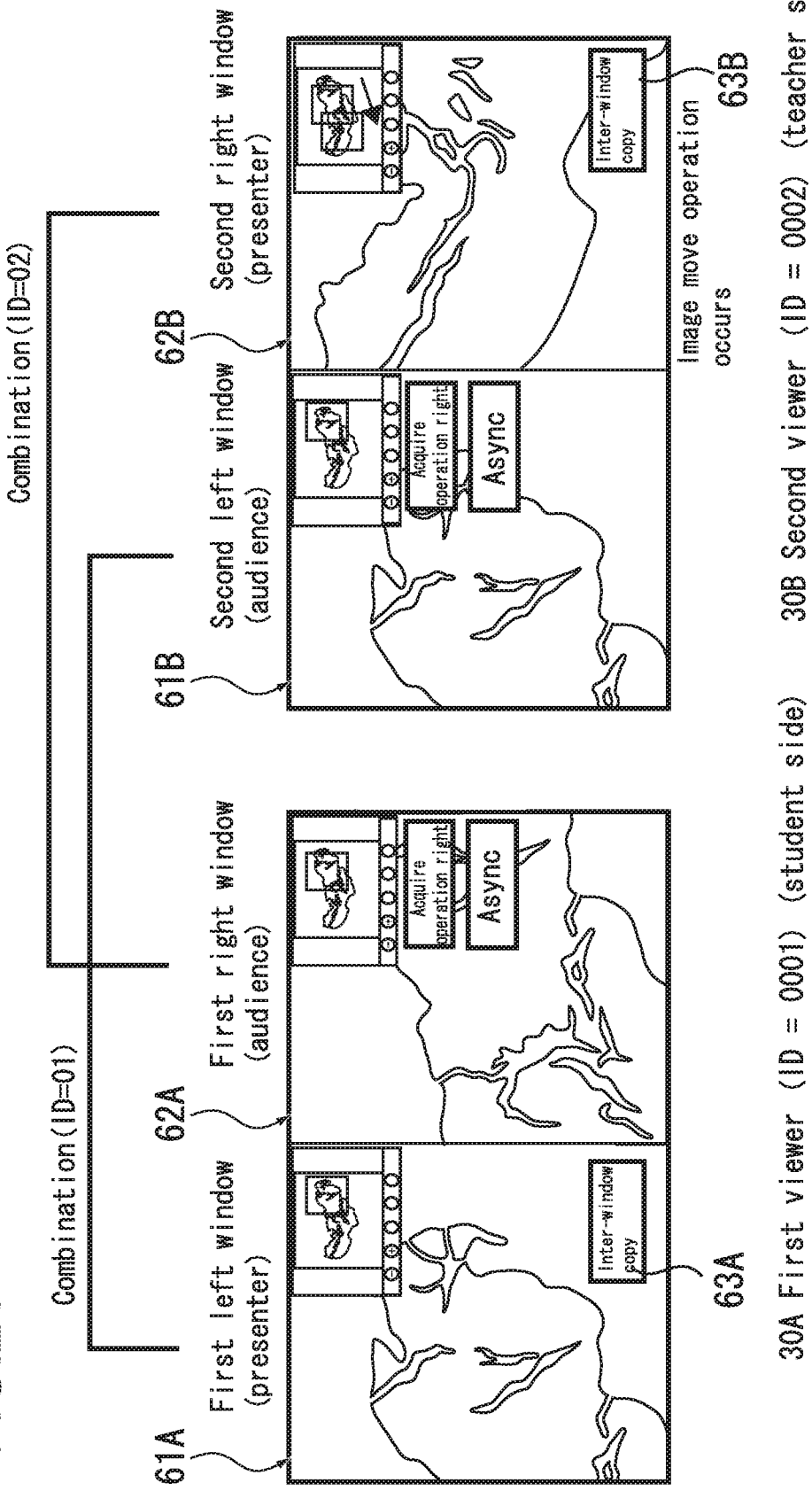
FIG. 21 is a diagram showing the state where a moving operation is performed with respect to the image in a second right window (presenter) of the second viewer.
Figure 22:
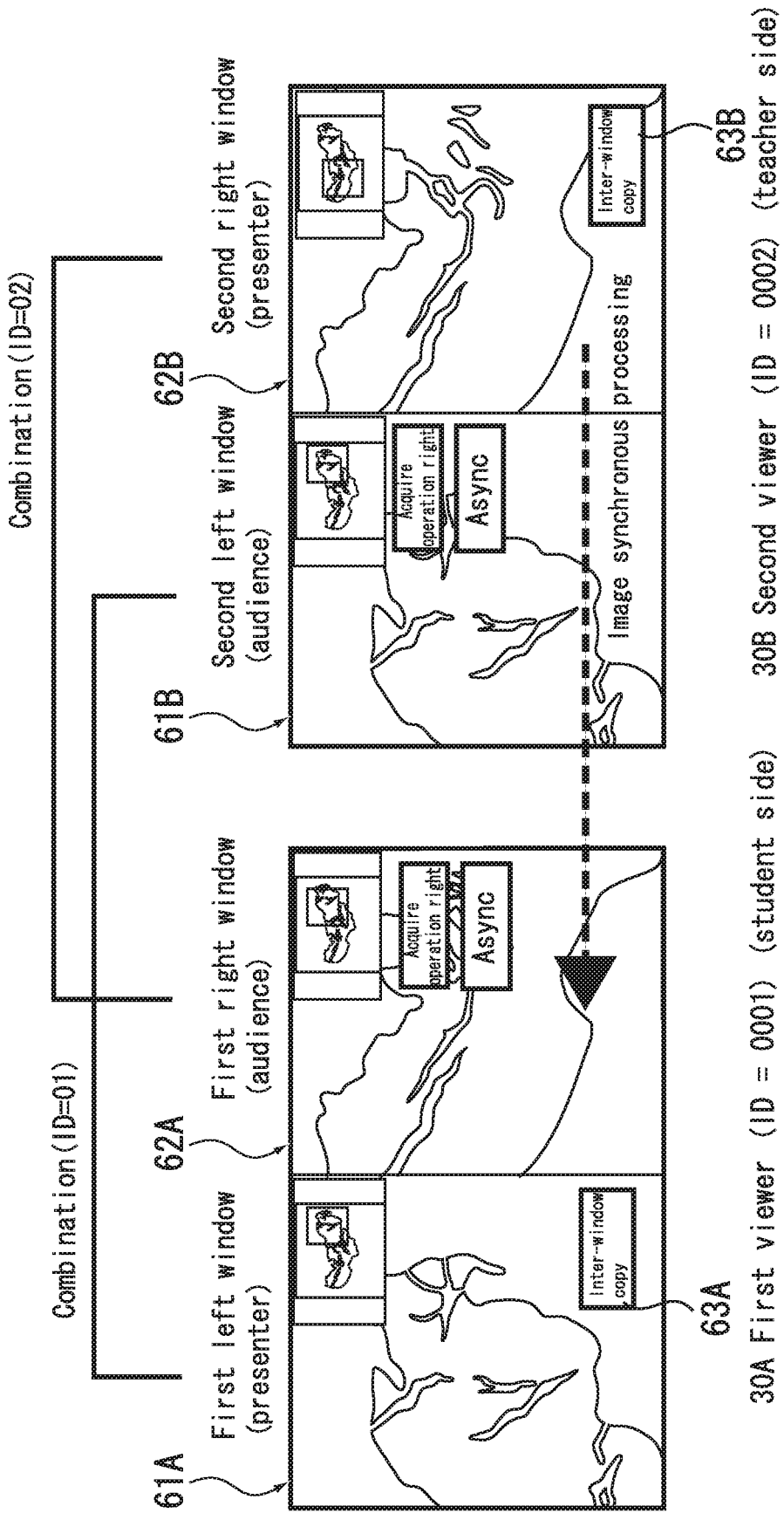
FIG. 22 is a diagram showing the state where image synchronous processing is performed between the second right window of the second viewer and the first right window of the first viewer.

FIG. 21 shows the result of moving operations on the image in the second right window 62B (presenter) of the second viewer 30B by a teacher. Moving operations are input in the image in the second right window 62B (presenter). Because of the moving operations, as shown in FIG. 22, the image in the first right window 62A (audience) of the first viewer 30A is updated based on the synchronous processing.

Figure 23:
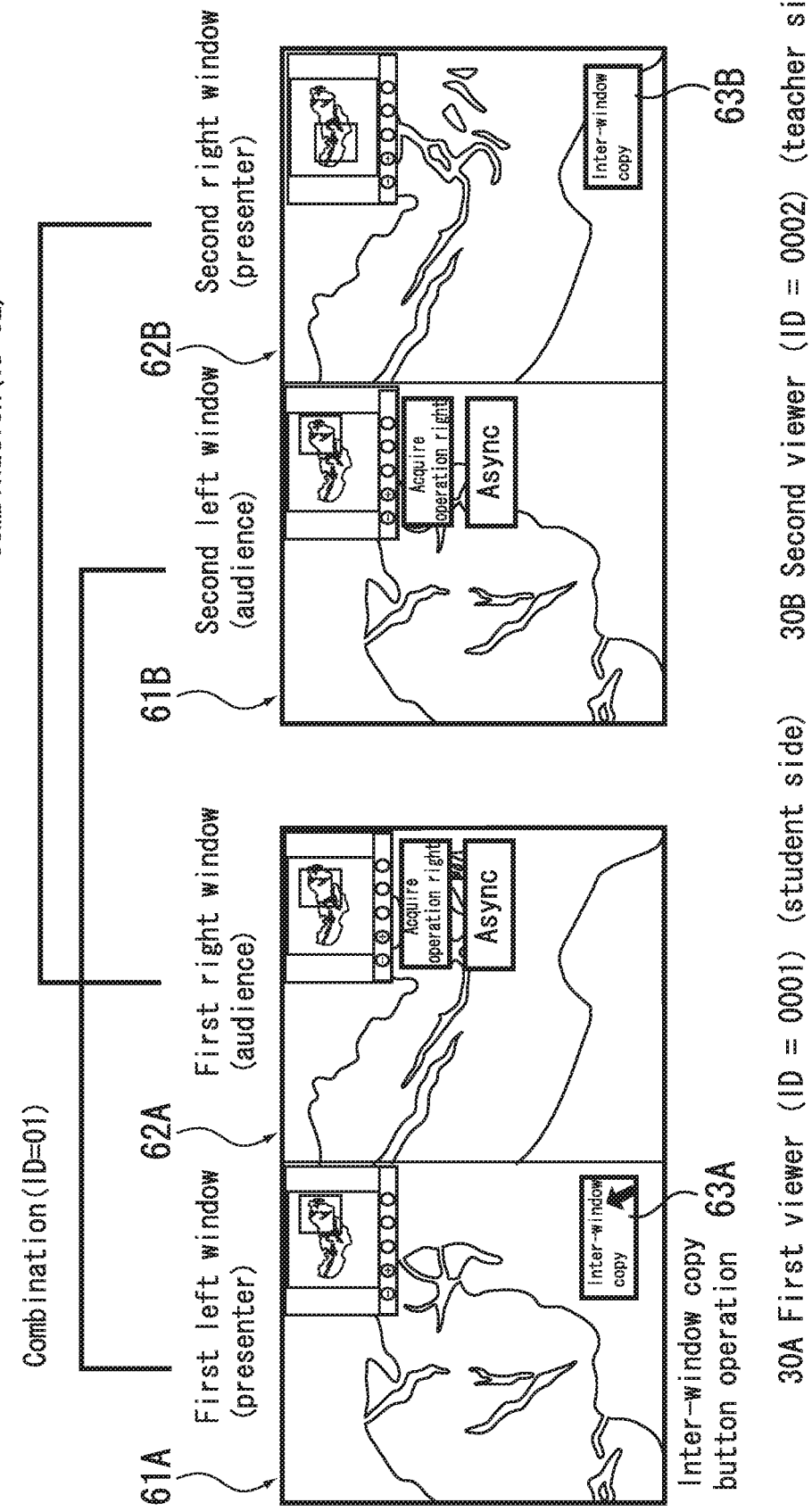
FIG. 23 is a diagram showing the state where an inter-window copy button in a left window of the first viewer is operated.

Here, a student wishes to confirm the area in the vicinity of the image, which is displayed in the first right window 62A, and the details of the image by using the first left window 61A (presenter) of the first viewer 30A. In this case, as shown in FIG. 23, the student operates the inter-window copy button 63A in the first left window 61A by using the input unit 31A (H1 in FIG. 9).

Figure 24:
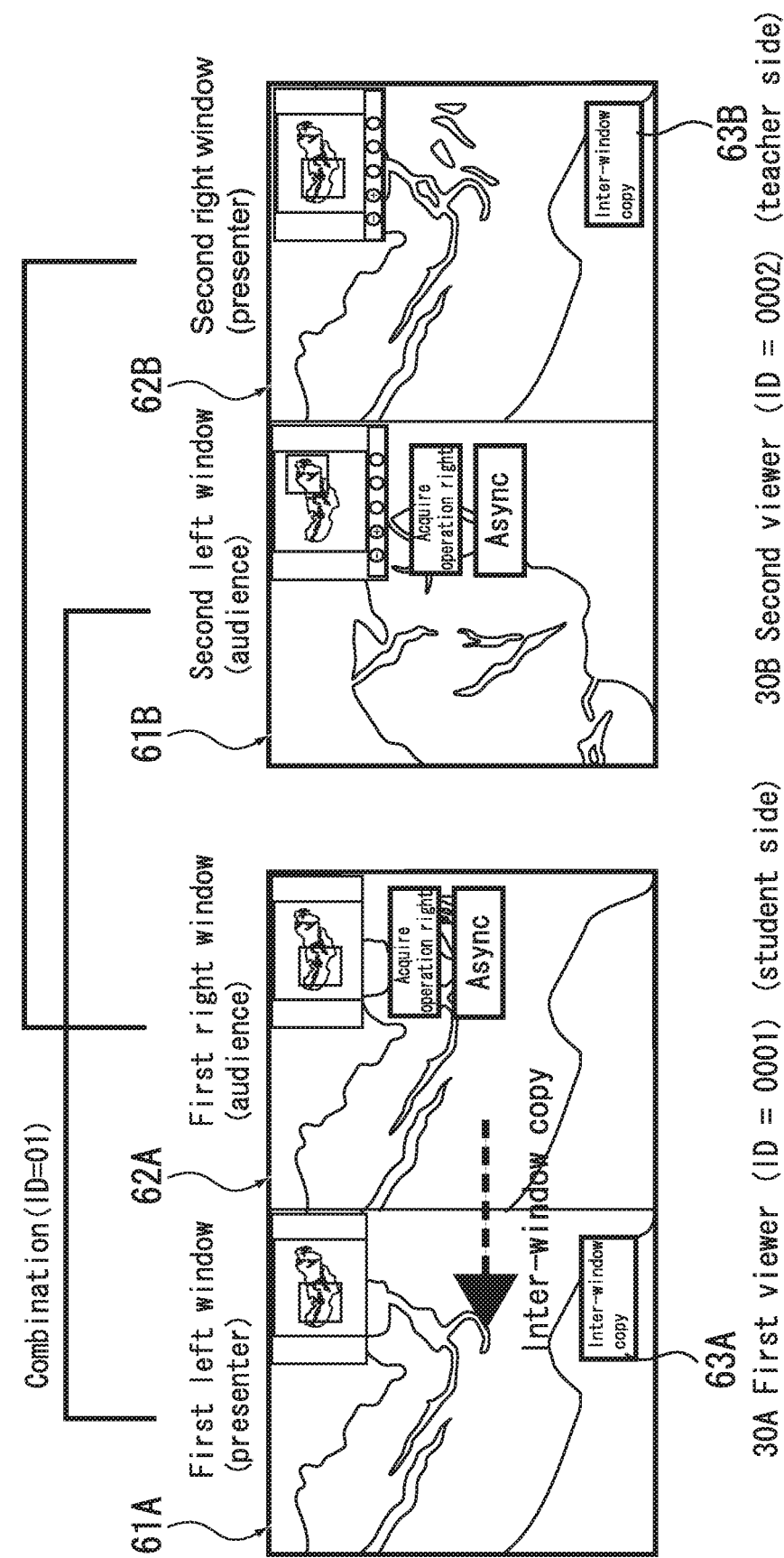
FIG. 24 is a diagram showing an inter-window image copy processing state.

The viewer controller 37A of the first viewer 30A determines that the inter-window copy button 63A is operated. In this case, the viewer controller 37A obtains the copy of the image data displayed in the first right window 62A (H2 in FIG. 9). Then, as shown in FIG. 24, the viewer controller 37A replaces the image in the first left window 61A with the obtained image data (H3 in FIG. 9).

In this manner, the area of the image in the window, the operation right to which is granted to the teacher at present, that is, the image on which the teacher gives an explanation at present, may be promptly displayed in the window, the operation right to which is granted to the student side. Therefore, the student may swiftly start to confirm the area in the vicinity of the image, to which the teacher pays attention at present, and the details of the image, by using the window, the operation right to which is granted to the student side.

Note that, the viewer controller 37A may obtain the image data displayed in the first right window 62A by copying image data in the memory of the first viewer 30A. Alternatively, the viewer controller 37A may obtain the image data by accessing the image server 10.

Further, the viewer controller 37A of the first viewer 30A updates the image in the first left window 61A. After that, the viewer controller 37A calculates image location information on the updated image. The viewer controller 37A sends a synchronous commission to the synchronous server 20 (H4 in FIG. 9). The synchronous commission includes the image location information, the viewer ID, and the window ID of the first left window 61A.

The synchronous server 20 extracts the image location information, the viewer ID, and the window ID from the received synchronous commission. The synchronous server 20 sends a synchronous request including those pieces of information to the second viewer 30B (H5 in FIG. 9).

Figure 25:
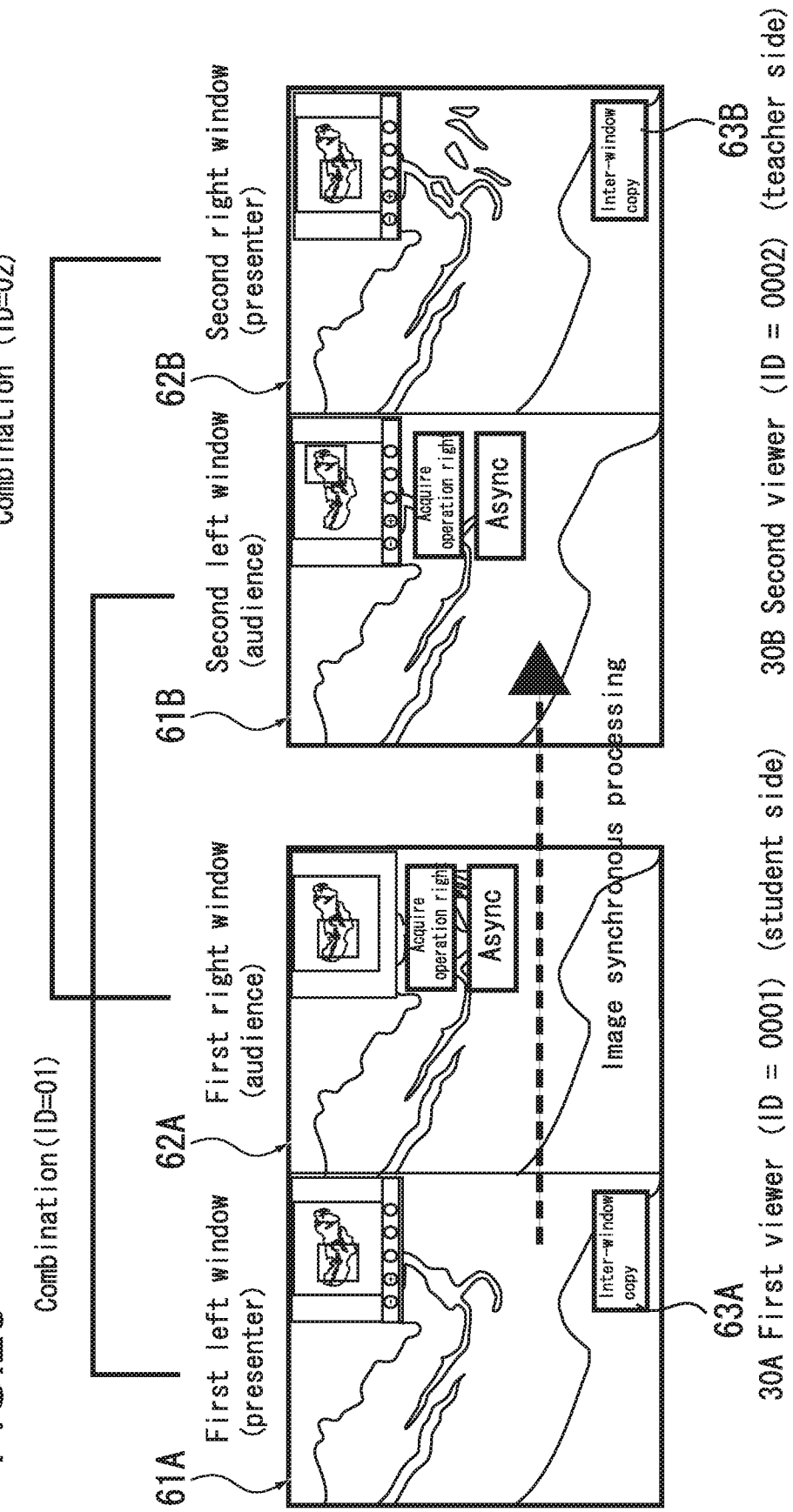
FIG. 25 is a diagram showing the synchronous processing after the inter-window image copy processing.

Based on the location information and the window ID included in the received synchronous request, as shown in FIG. 25, the viewer controller 37B of the second viewer 30B updates the image in the second left window 61B (H6 in FIG. 9).

[General Computer]

Next, the configuration of a general computer, which may be used as the image server 10, the synchronous server 20, or the viewer 30A, 30B, will be described.

Figure 10:
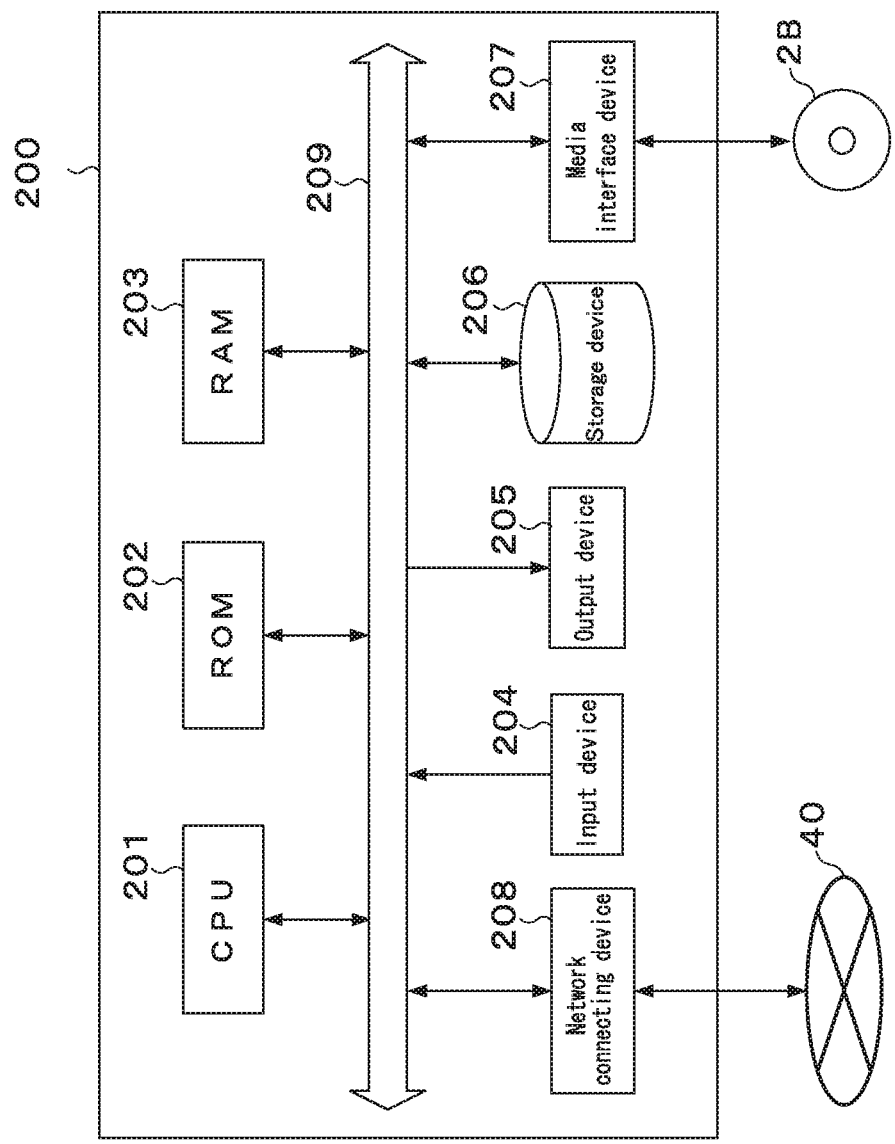
FIG. 10 is a diagram showing the hardware configuration of a general computer.

FIG. 10 is a diagram showing the hardware configuration of a general computer 200.

As shown in FIG. 10, the computer 200 includes a CPU (Central Processing Unit) 201, a ROM (Read Only Memory) 202, and a RAM (Random Access Memory) 203. The computer 200 further includes an input device 204, an output device 205, a storage device 206, a media interface device 207, a network connecting device 208, and a bus 209 connecting them to each other.

The CPU 201 functions as an arithmetic processing unit and a control unit. The CPU 201 controls the entire behaviors of the computer 200 based on various programs. The ROM 202 stores the programs, arithmetic parameters, and the like to be used by the CPU 201. The RAM 203 temporarily stores the programs executed by the CPU 201, parameters arbitrarily change during the execution of the programs, and the like.

The synchronous processing unit 25 of the synchronous server 20, the viewer controllers 37A, 37B of the viewers 30A, 30B, and the like are implemented by, for example, the CPU 201, the programs stored in the ROM 202, the working area of the RAM 203, and the like in the hardware configuration of the computer 200.

The input device 204 includes input means, an input control circuit, and the like. A user inputs information by using the input means such as a mouse, a keyboard, a touchpad, buttons, a microphone, switches, a lever, and the like. The input control circuit creates input signals based on instructions input by a user, outputs the signals to the CPU 201, and the like. By operating the input device 204, a user of the computer 200 may input various data in the CPU 201, and may input processing-behavior instructions in the CPU 201.

The output device 205 includes a display device such as, for example, a CRT (Cathode Ray Tube) display device, a liquid crystal display (LCD) device, an OLED (Organic Light Emitting Diode) device, or the like. Further, the output device 205 includes sound output devices such as a speaker, headphone, and the like.

The storage device 206 is a device for storing the programs and user data. The storage device 206 includes a storage medium, a reader/writer that reads/writes data from/in the storage medium, and the like. The storage device 206 consists of, for example, a HDD (Hard Disk Drive), an SSD (Solid State Drive), or the like.

The media interface device 207 is a reader/writer for a storage medium. The media interface device 207 reads/writes data from/in a loaded removal recording medium 2A such as a magnetic disk, an optical disk, a magneto-optical disk, a semiconductor memory, or the like.

The network connecting device 208 is, for example, an interface connecting the computer 200 to the network 40. The network connecting device 208 may be a device for a wireless LAN (Local Area Network), a device for a wireless USB, or a wired communication device performing wired communication.

Modified Example 1

The image synchronous processing between two viewers has been described. However, it is needless to say that the present disclosure may be applied to a case where three or more viewers are connected to each other. That is, the operation right is granted to one window, as a presenter, of three or more window combinations in the correspondence relation of three or more viewers. Operations on the image in the presenter window may be reflected in the other audience windows.

Modified Example 2

Figure 11:
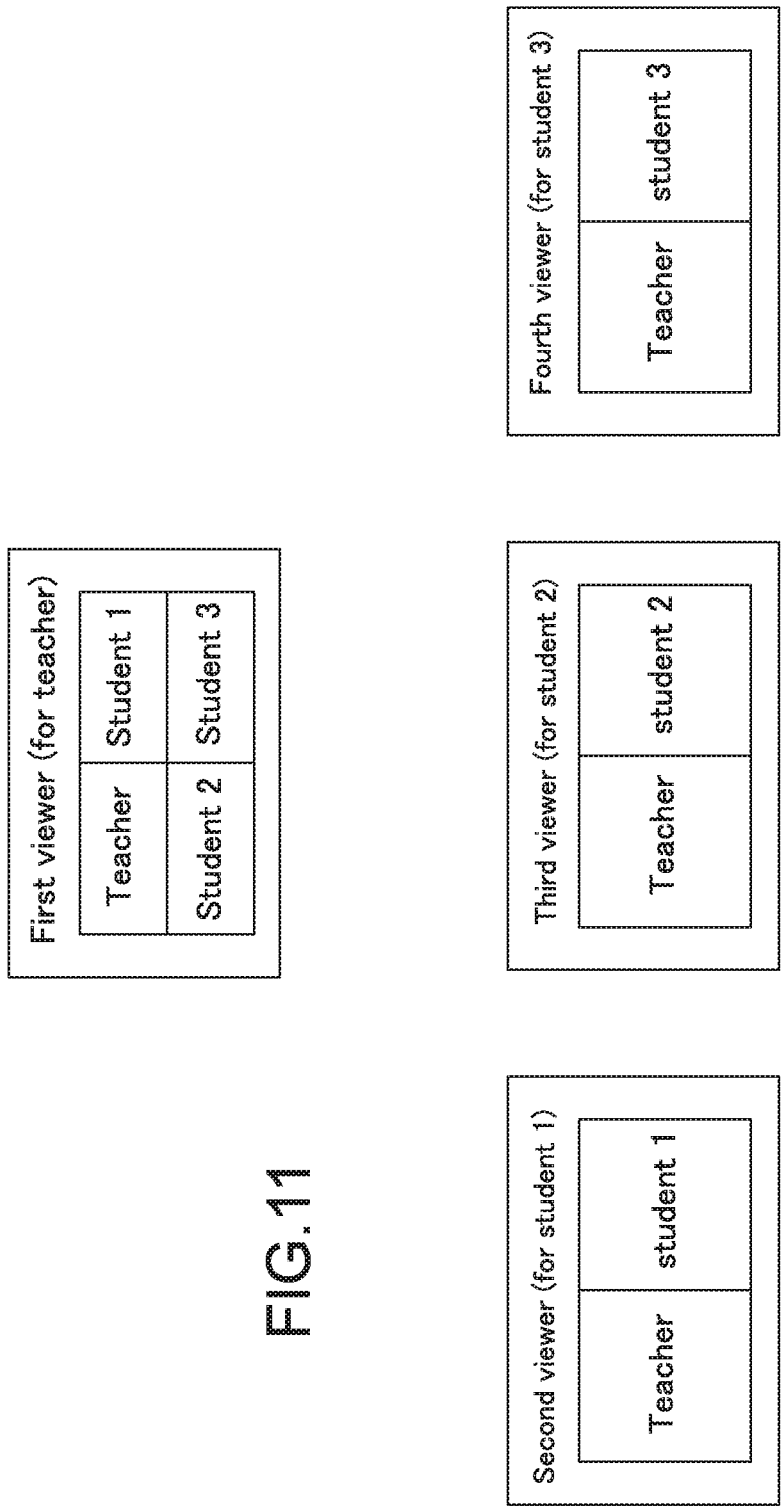
FIG. 11 is a diagram for explaining a modified example of the embodiment of the present disclosure.

Further, in a case where three or more viewers are connected to each other, each viewer does not necessarily display the windows of all the viewers. For example, a teacher-side viewer is connected to a plurality of student-side viewers. In this case, as shown in FIG. 11, the teacher-side viewer may display the window, the operation right to which is granted to the teacher, and a plurality of windows of all the students as audience windows. A student-side viewer may display the window, the operation right to which is granted to the student himself, and the window of the teacher as an audience window. As described above, the window display is selectively controlled for each viewer. The selective control may be implemented by using, for example, a table that controls information for selecting a window to be displayed as an audience for each viewer (for example, combination of viewer ID and window ID, etc.), for example.

Note that, the present disclosure may employ the following configurations.

According to an embodiment, an information processing system includes a first information processing apparatus configured to display a first synchronous image in a first window, the first window having an operation right, and includes a second information processing apparatus having a synchronous state or an asynchronous state. The second information processing apparatus is configured to: display a second synchronous image; in response to a first request, switch from the synchronous state to the asynchronous state; and in response to a second request, switch from the asynchronous state to the synchronous state.

In the information processing system, the second synchronous image is the same as the first synchronous image when the second information processing apparatus has the synchronous state.

In the information processing system, the second information processing apparatus is configured to, when the second information processing apparatus has the asynchronous state, enable a user to operate an input device to control an image displayed by the second information processing apparatus.

In the information processing system, in response to a third request, the operation right is moved from the first information processing apparatus to the second information processing apparatus.

In the information processing system, the second information processing apparatus is configured to, in response to a third request, transmit an operation right acquisition request.

In the information processing system, the second information processing apparatus is configured to receive an operation right acquisition reply.

In the information processing system, the second information processing apparatus is configured to display the second synchronous image in a second window.

In the information processing system of claim 1, the first information processing apparatus is configured to display a third synchronous image in a third window, the third window having a second operation right. The second information processing apparatus is configured to display a fourth synchronous image in a fourth window.

In the information processing system, in response to a third request, the second operation right is moved from the third window to the fourth window of the second information processing apparatus.

According to another embodiment, a method of operating an information processing system is provided. The method includes: causing a first information processing apparatus to display a first synchronous image in a first window, the first window having an operation right; causing a second information processing apparatus to display a second synchronous image, the second information processing apparatus having a synchronous state or an asynchronous state; in response to a first request, causing the second information processing apparatus to switch from the synchronous state to the asynchronous state; and in response to a second request, causing the second information processing apparatus to switch from the asynchronous state to the synchronous state.

In the method, the second synchronous image is the same as the first synchronous image when second information processing apparatus has the synchronous state.

The method further includes causing the second information processing apparatus to, when the second information processing apparatus has the asynchronous state, enable a user to operate an input device to control an image displayed by the second information processing apparatus.

In the method, in response to a third request, the operation right is moved from the first information processing apparatus to the second information processing apparatus.

The method further includes causing the second information processing to, in response to a third request, transmit an operation right acquisition request.

The method further includes causing the second information processing apparatus to receive an operation right acquisition reply.

The method further includes causing the second information processing apparatus to display the second synchronous image in a second window.

The method further includes causing the first information processing apparatus to display a third synchronous image in a third window, the third window having a second operation right. And the method includes causing the second information processing apparatus to display a fourth synchronous image in a fourth window.

In the method, in response to a third request, the second operation right is moved from the third window to the fourth window of the second information processing apparatus.

In another embodiment, an information processing apparatus includes a processor and a memory device storing instructions. When executed by the processor, the instructions cause the processor to: receive, from a first information processing apparatus, an asynchronous request; in response to receiving the asynchronous request, for the first information processing apparatus, set a flag; thereafter, receive from the first information processing apparatus, a synchronous request; and in response to receiving the synchronous request, reset the flag.

In the information processing apparatus, the instructions, when executed by the processor, cause the processor to receive, from the first information processing apparatus, an operation right acquisition request; in response to receiving the operation right request, transmit an operation right abandonment request to a second information processing request; thereafter, receive an operation right abandonment reply from the second information processing apparatus; and in response to receiving the operation right abandonment reply, transmit an operation right acquisition reply to the first information processing apparatus.

In the information processing apparatus, the operation right acquisition request includes data representative of a window identification.

According to another embodiment, an information processing apparatus includes a processor, a display device, and a memory device storing instructions. When executed by the processor, the instructions cause the processor, in cooperation with the display device, to: display a synchronous image; in response to a first request, switch from a synchronous state to an asynchronous state; and in response to a second request, switch from the asynchronous state to the synchronous state.

In the information processing apparatus, the synchronous image is the same as another synchronous image being displayed by another information processing apparatus when the information processing apparatus has the synchronous state.

In the information processing apparatus, the instructions, when executed by the processor, cause the processor to enable a user to operate an input device to control a displayed image when the information processing apparatus has the asynchronous state.

In the information processing apparatus, the instructions, when executed by the processor, cause the processor to receive an operation right.

In the information processing apparatus, the instructions, when executed by the processor, cause the processor to, in response to a third request, transmit an operation right acquisition request.

In the information processing apparatus, the instructions, when executed by the processor, cause the processor to receive an operation right acquisition reply.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. An information processing apparatus comprising:
   a processor; and
   a memory device storing instructions that cause the processor to:
      control a first display device to display a first area of a medical image and a second area of the same medical image, wherein the second area has a different zoom factor than the first area;
      control the first display device to change a first part of the first area based on the second area; and
      control the first display device to change a second part of the first area based on a third area of the same medical image displayed in a second display device, wherein the third area has a different zoom factor than the first area, and the second area has different image location information than the third area.

2. The information processing apparatus of claim 1, wherein the medical image includes at least one of a pathological image, a microscopic image, and an X-ray image.

3. The information processing apparatus of claim 1, wherein a first frame and a second frame are displayed on the first display device.

4. The information processing apparatus of claim 1, wherein the instructions further cause the processor to adjust the first area based on operation information input by a user.

5. The information processing apparatus of claim 4, wherein the operation information includes at least one of a move operation, a zoom operation, and a rotation operation.

6. A method comprising:
   controlling a first display device to display a first area of a medical image and a second area of the same medical image, wherein the second area has a different zoom factor than the first area;
   controlling the first display device to change a first part of the first area based on the second area; and
   controlling the first display device to change a second part of the first area based on a third area of the same medical image displayed in a second display device, wherein the third area has a different zoom factor than the first area, and the second area has different image location information than the third area.

7. The method of claim 6, wherein the medical image includes at least one of a pathological image, a microscopic image, and an X-ray image.

8. The method of claim 6, wherein a first frame and a second frame are displayed on the first display device.

9. The method of claim 6, further comprising adjusting the first area based on operation information input by a user.

10. The method of claim 9, wherein the operation information includes at least one of a move operation, a zoom operation, and a rotation operation.

11. A non-transitory computer readable medium storing instructions, which when executed by a processor, cause the processor to:
   control a first display device to display a first area of a medical image and a second area of the same medical image, wherein the second area has a different zoom factor than the first area;
   control the first display device to change a first part of the first area based on the second area; and
   control the first display device to change a second part of the first area based on a third area of the same medical image displayed in a second display device, wherein the third area has a different zoom factor than the first area, and the second area has different image location information than the third area.

12. The non-transitory computer readable medium of claim 11, wherein the medical image includes at least one of a pathological image, a microscopic image, and an X-ray image.

13. The non-transitory computer readable medium of claim 11, wherein a first frame and a second frame are displayed on the first display device.

14. The non-transitory computer readable medium of claim 11, wherein the instructions further cause the processor to adjust the first area based on operation information input by a user.

15. The non-transitory computer readable medium of claim 14, wherein the operation information includes at least one of a move operation, a zoom operation, and a rotation operation.

* * * * *